(12) United States Patent
Miyake et al.

(10) Patent No.: US 7,425,536 B2
(45) Date of Patent: Sep. 16, 2008

(54) FELINE HEPATOCYTE GROWTH FACTOR

(75) Inventors: Masashi Miyake, Fukushima (JP);
Shigehiro Iwabuchi, Fukushima (JP);
Yasuyuki Suzuta, Fukushima (JP)

(73) Assignee: Nippon Zenyaku Kogyo Ltd. (JP)

( * ) Notice: Subject to any disclaimer, the term of this patent is extended or adjusted under 35 U.S.C. 154(b) by 0 days.

(21) Appl. No.: 11/450,056

(22) Filed: Jun. 9, 2006

(65) Prior Publication Data

US 2006/0217314 A1    Sep. 28, 2006

Related U.S. Application Data

(62) Division of application No. 10/297,158, filed as application No. PCT/JP01/04559 on Dec. 2, 2002, now Pat. No. 7,125,688.

(30) Foreign Application Priority Data

May 31, 2000    (JP) .............................. 2000-163185

(51) Int. Cl.
*A61K 38/00*    (2006.01)
(52) U.S. Cl. .......................................... 514/2; 530/399
(58) Field of Classification Search ........................ None
See application file for complete search history.

(56) References Cited

U.S. PATENT DOCUMENTS

| 5,342,831 A | * | 8/1994 | Nakamura et al. | ............. 514/12 |
| 5,871,959 A |   | 2/1999 | Rong et al. |  |
| 6,699,837 B2 | * | 3/2004 | Nakamura | .................... 514/12 |

FOREIGN PATENT DOCUMENTS

| EP | 0461560 A1 |   | 6/1991 |
| EP | 0 859 009 A2 |   | 8/1998 |
| WO | EP 0 550 296 | * | 7/1993 |
| WO | WO94/01548 | * | 1/1994 |

OTHER PUBLICATIONS

Kobayashi et al. Locus AB046610, Jan. 27, 2001. Accessed Mar. 22, 2005 (see attached computer printout).*

"Molecular Cloning of Feline Hepatocyte Growth Factor (HGF) cDNA", J. Vet. Med. Sci., vol. 63, No. 2, pp. 211-214, 2001.
"Deduced primary structure of rat hepatocyte growth factor and expression of the MRNA to rat tissues", Cell Biology, vol. 87, pp. 3200-3204, 1990.
Nakamura, et al., Molecular Cloning and Expression of Human Hepatocyte Growth Factor, Nature, Macmillan Journals Ltd., London, vol. 342, Nov. 23, 1989, pp. 440-443, XP000652120.
Okigaki, et al., Functional Characterization of Human Hepatocyte Growth Factor Mutants Obtained by Deletion of Structural Domains, Biochemistry, vol. 31, No. 40, 1992, pp. 9555-9561, XP002279003.
"Characterization of the Scatter Factor/Hepatocyte Growth Factor Gene Promoter" The Journal of Biological Chemistry, vol. 270, No. 2, Jan. 1995, pp. 830-836.
"Primary structure of rat hepatocyte growth factor and induction of its MRNA during liver regeneration following hepatic injury", Eur. J. Biochem. vol. 193., pp. 375-381, 1990.
"Identification of mouse mammary fibroblast-derived mammary growth factor as hepatocyte growth factor", Biochemical and Biophysical Research Communications, vol. 199, No. 2, pp. 772-779, 1994.
"Molecular cloning and sequence analysis of cDNA for Human Hepatocyte growth factor", Biochemical and Biophysical Research Communications, vol. 163, No. 2, pp. 967-973, 1989.
Patent Abstracts of Japan, Publication No. 3-204899, corresponding to JP 3-204899 A, Otsuka Pharmaceutical Co., Ltd., Sep. 6, 1991.
"Molecular cloning and characterization of cDNA encoding mouse hepatocyte growth factor", Biochimica et Biophysica Acta, vol. 1216, pp. 299-303, 1993.
Molecular Cloning and Chromosomal Mapping of Feline p53 Tumor Suppressor Gene, J. Vet. Med. Sci., vol. 55, No. 5, pp. 801-805, 1993.

* cited by examiner

*Primary Examiner*—Dong Jiang
(74) *Attorney, Agent, or Firm*—Lucas & Mercanti, LLP.

(57) ABSTRACT

A feline hepatocyte growth factor gene and a 15 base pairs-deleted feline hepatocyte growth factor gene. These genes encode a protein having an amino acid sequence shown in SEQ ID NO: 2 or 4.

The feline hepatocyte growth factor and the 5 amino acids-deleted feline hepatocyte growth factor are useful for the treatment of liver diseases, kidney diseases, lung diseases, digestive diseases, cardiocirculatory diseases or cranial nerve diseases.

3 Claims, 8 Drawing Sheets fHGF PRODUCED IN COS CELL dfHGF PRODUCED IN COS CELL pCI-neo fHGF PRODUCED IN CHO CELL dfHGF PRODUCED IN CHO CELL pCI-neo

1. SILKWORM BODY FLUID INFECTED WITH fHGF RECOMBINANT VIRUS

2. SILKWORM BODY FLUID INFECTED WITH NON-RECOMBINANT VIRUS fHGF PRODUCED
IN SILKWORM BODY FLUID dfHGF PRODUCED
IN SILKWORM BODY FLUID

SILKWORM BODY FLUID INFECTED
WITH NON-RECOMBINANT VIRUS

1. SUPERNATANT OF Sf9 CELL INFECTED WITH fHGF RECOMBINANT VIRUS

2. SUPERNATANT OF Sf9 CELL INFECTED WITH NON-RECOMBINANT VIRUS fHGF PRODUCED IN Sf9 CELL dfHGF PRODUCED IN Sf9 CELL

Sf9 CELL INFECTED
WITH NON-RECOMBINANT VIRUS

SEQUENCE LISTING

```
<160> NUMBER OF SEQ ID NOS: 18

<210> SEQ ID NO 1
<211> LENGTH: 2187
<212> TYPE: DNA
<213> ORGANISM: Felis sp.
<220> FEATURE:
<221> NAME/KEY: CDS
<222> LOCATION: (1)..(2187)

<400> SEQUENCE: 1 atg tgg gtg acc aaa ctt ctt cca gtc ctg ctg ctg cag cac gtc ctc      48
Met Trp Val Thr Lys Leu Leu Pro Val Leu Leu Leu Gln His Val Leu
 1               5                  10                  15
```

```
ctc cac ctc ctt ctg ctt ccc atc ccc tat gca gaa gga cag aag aaa      96
Leu His Leu Leu Leu Leu Pro Ile Pro Tyr Ala Glu Gly Gln Lys Lys
            20                  25                  30 aga aga aac aca ctt cat gaa ttc aaa aag tca gca aag act act cta     144
Arg Arg Asn Thr Leu His Glu Phe Lys Lys Ser Ala Lys Thr Thr Leu
        35                  40                  45 att aaa gaa gac cca tta ctg aag ata aaa aca aaa aaa atg aac act     192
Ile Lys Glu Asp Pro Leu Leu Lys Ile Lys Thr Lys Lys Met Asn Thr
    50                  55                  60 gca gac caa tgt gcc aat aga tgt att agg aat aaa gga ctt cca ttc     240
Ala Asp Gln Cys Ala Asn Arg Cys Ile Arg Asn Lys Gly Leu Pro Phe
65                  70                  75                  80 act tgc aag gcc ttt gtt ttt gat aaa gca agg aaa cga tgc ctc tgg     288
Thr Cys Lys Ala Phe Val Phe Asp Lys Ala Arg Lys Arg Cys Leu Trp
                85                  90                  95 ttc cct ttc aat agc atg aca agt gga gtg aaa aaa gag ttt ggt cat     336
Phe Pro Phe Asn Ser Met Thr Ser Gly Val Lys Lys Glu Phe Gly His
            100                 105                 110 gaa ttc gat ctc tat gaa aac aaa gac tac att aga aac tgc atc att     384
Glu Phe Asp Leu Tyr Glu Asn Lys Asp Tyr Ile Arg Asn Cys Ile Ile
        115                 120                 125 ggc aaa gga ggt agc tac aag gga aca gta tct atc act aag agt ggc     432
Gly Lys Gly Gly Ser Tyr Lys Gly Thr Val Ser Ile Thr Lys Ser Gly
    130                 135                 140 atc aaa tgc cag cct tgg aat tct atg ata cca cat gaa cac agc ttt     480
Ile Lys Cys Gln Pro Trp Asn Ser Met Ile Pro His Glu His Ser Phe
145                 150                 155                 160 ttg cct tcg agc tat cgg ggt aaa gac cta cag gaa aac tac tgt cga     528
Leu Pro Ser Ser Tyr Arg Gly Lys Asp Leu Gln Glu Asn Tyr Cys Arg
                165                 170                 175 aat cct cga ggg gaa gaa ggg gga cct tgg tgt ttc aca agc aat cca     576
Asn Pro Arg Gly Glu Glu Gly Gly Pro Trp Cys Phe Thr Ser Asn Pro
            180                 185                 190 gag gta cgc tac gaa gtc tgt gac att cct cag tgt tca gaa gtt gaa     624
Glu Val Arg Tyr Glu Val Cys Asp Ile Pro Gln Cys Ser Glu Val Glu
        195                 200                 205 tgc atg acc tgc aat ggg gaa agt tat cga ggt ccc atg gat cat aca     672
Cys Met Thr Cys Asn Gly Glu Ser Tyr Arg Gly Pro Met Asp His Thr
    210                 215                 220 gaa tca ggc aag att tgt cag cgc tgg gat cgt cag aca cca cac cgg     720
Glu Ser Gly Lys Ile Cys Gln Arg Trp Asp Arg Gln Thr Pro His Arg
225                 230                 235                 240 cac aaa ttc ttg cca gaa aga tat ccc gac aag ggc ttt gat gat aat     768
His Lys Phe Leu Pro Glu Arg Tyr Pro Asp Lys Gly Phe Asp Asp Asn
                245                 250                 255 tat tgc cgc aat cct gat ggc aag ccg agg cca tgg tgc tat act ctt     816
Tyr Cys Arg Asn Pro Asp Gly Lys Pro Arg Pro Trp Cys Tyr Thr Leu
            260                 265                 270 gac cct gac acc ccc tgg gag tac tgt gca att aaa atg tgc gct cac     864
Asp Pro Asp Thr Pro Trp Glu Tyr Cys Ala Ile Lys Met Cys Ala His
        275                 280                 285 agt act atg aat gac aca gat gtg cct atg gaa aca act gaa tgc att     912
Ser Thr Met Asn Asp Thr Asp Val Pro Met Glu Thr Thr Glu Cys Ile
    290                 295                 300 cag ggt caa gga gaa ggt tac cgg ggc acc atc aac tcc atc tgg aat     960
Gln Gly Gln Gly Glu Gly Tyr Arg Gly Thr Ile Asn Ser Ile Trp Asn
305                 310                 315                 320 gga gtt cca tgt cag cgt tgg gat tcc cag tat cct cac cag cat gac    1008
Gly Val Pro Cys Gln Arg Trp Asp Ser Gln Tyr Pro His Gln His Asp
                325                 330                 335
```

```
ata act cct gaa aat ttc aag tgc aag gac cta cga gaa aat ttt tgc     1056
Ile Thr Pro Glu Asn Phe Lys Cys Lys Asp Leu Arg Glu Asn Phe Cys
            340                 345                 350 cga aat cca gat gga gct gag tca ccc tgg tgt ttt acc act gat cca     1104
Arg Asn Pro Asp Gly Ala Glu Ser Pro Trp Cys Phe Thr Thr Asp Pro
        355                 360                 365 aac atc cga gtt ggc tac tgc tcc caa att cca aaa tgt gat gtg tcg     1152
Asn Ile Arg Val Gly Tyr Cys Ser Gln Ile Pro Lys Cys Asp Val Ser
    370                 375                 380 agt gga caa gat tgt tat cgt ggg aat ggc aaa aat tat atg ggc aat     1200
Ser Gly Gln Asp Cys Tyr Arg Gly Asn Gly Lys Asn Tyr Met Gly Asn
385                 390                 395                 400 tta tcc aaa aca cga tct gga cta aca tgt tca atg tgg gag aag aac     1248
Leu Ser Lys Thr Arg Ser Gly Leu Thr Cys Ser Met Trp Glu Lys Asn
            405                 410                 415 atg gaa gac tta cac agg cat atc ttc tgg gaa cca gat gct agt aag     1296
Met Glu Asp Leu His Arg His Ile Phe Trp Glu Pro Asp Ala Ser Lys
        420                 425                 430 ctg aat aag aat tac tgc cgg aat cct gat gat gat gcc cat ggc ccc     1344
Leu Asn Lys Asn Tyr Cys Arg Asn Pro Asp Asp Asp Ala His Gly Pro
    435                 440                 445 tgg tgt tac acg gga aat cct ctc att cca tgg gat tat tgt cct att     1392
Trp Cys Tyr Thr Gly Asn Pro Leu Ile Pro Trp Asp Tyr Cys Pro Ile
450                 455                 460 tct cgt tgt gaa ggt gat acc aca cct aca ata gtc aat tta gac cat     1440
Ser Arg Cys Glu Gly Asp Thr Thr Pro Thr Ile Val Asn Leu Asp His
465                 470                 475                 480 ccc gta ata tct tgt gcc aaa aca aaa caa ctg cga gtt gta aat gga     1488
Pro Val Ile Ser Cys Ala Lys Thr Lys Gln Leu Arg Val Val Asn Gly
            485                 490                 495 atc cca acg cgg aca aat gta gga tgg atg gtt agt ttg aaa tac aga     1536
Ile Pro Thr Arg Thr Asn Val Gly Trp Met Val Ser Leu Lys Tyr Arg
        500                 505                 510 aat aaa cat atc tgt gga gga tca ttg ata aag gaa agt tgg att ctt     1584
Asn Lys His Ile Cys Gly Gly Ser Leu Ile Lys Glu Ser Trp Ile Leu
    515                 520                 525 acc gca aga caa tgt ttc cct tct cga aac aaa gac ttg aaa gat tac     1632
Thr Ala Arg Gln Cys Phe Pro Ser Arg Asn Lys Asp Leu Lys Asp Tyr
530                 535                 540 gaa gct tgg ctt ggg att cat gat gtc cac gga aga gga gat gag aaa     1680
Glu Ala Trp Leu Gly Ile His Asp Val His Gly Arg Gly Asp Glu Lys
545                 550                 555                 560 cgc aaa cag gtt cta aat gtg tcc cag ctg gta tat ggg cct gaa ggg     1728
Arg Lys Gln Val Leu Asn Val Ser Gln Leu Val Tyr Gly Pro Glu Gly
            565                 570                 575 tca gat ctg gta tta ctg aag ctt gct agg cct gct gtc ctg gat gat     1776
Ser Asp Leu Val Leu Leu Lys Leu Ala Arg Pro Ala Val Leu Asp Asp
        580                 585                 590 ttt gtt agt aca att gat tta cct aat tat gga tgc acc att cct gaa     1824
Phe Val Ser Thr Ile Asp Leu Pro Asn Tyr Gly Cys Thr Ile Pro Glu
    595                 600                 605 aaa acc act tgc agt gtt tat ggc tgg ggt tat act gga tca atc aac     1872
Lys Thr Thr Cys Ser Val Tyr Gly Trp Gly Tyr Thr Gly Ser Ile Asn
610                 615                 620 tct gat ggt cta tta cga gta gca cat ctc tat att atg ggg aat gag     1920
Ser Asp Gly Leu Leu Arg Val Ala His Leu Tyr Ile Met Gly Asn Glu
625                 630                 635                 640 aaa tgc agc caa tac cat caa ggg aag gtg act ctg aat gag tct gaa     1968
Lys Cys Ser Gln Tyr His Gln Gly Lys Val Thr Leu Asn Glu Ser Glu
```

```
                  645               650                 655
ata tgt gca ggt gcc gaa aat att gtg tca gga cca tgt gag gga gat    2016
Ile Cys Ala Gly Ala Glu Asn Ile Val Ser Gly Pro Cys Glu Gly Asp
                  660                 665                 670 tat ggt ggc cca ctt gtt tgt gaa caa cat aaa atg aga atg gtc ctt    2064
Tyr Gly Gly Pro Leu Val Cys Glu Gln His Lys Met Arg Met Val Leu
            675                 680                 685 ggt gtc att gtt cct ggt cgt gga tgt gcc att cca aat cgt cct ggc    2112
Gly Val Ile Val Pro Gly Arg Gly Cys Ala Ile Pro Asn Arg Pro Gly
        690                 695                 700 att ttt gtc cga gta gca tat tat gca aaa tgg ata cac aaa att ata    2160
Ile Phe Val Arg Val Ala Tyr Tyr Ala Lys Trp Ile His Lys Ile Ile
705                 710                 715                 720 tta aca tat aag ata cca cag tca tag                                2187
Leu Thr Tyr Lys Ile Pro Gln Ser
                725

<210> SEQ ID NO 2
<211> LENGTH: 728
<212> TYPE: PRT
<213> ORGANISM: Felis sp.

<400> SEQUENCE: 2

Met Trp Val Thr Lys Leu Leu Pro Val Leu Leu Leu Gln His Val Leu
 1               5                  10                  15

Leu His Leu Leu Leu Pro Ile Pro Tyr Ala Glu Gly Gln Lys Lys
            20                  25                  30

Arg Arg Asn Thr Leu His Glu Phe Lys Lys Ser Ala Lys Thr Thr Leu
        35                  40                  45

Ile Lys Glu Asp Pro Leu Leu Lys Ile Lys Thr Lys Lys Met Asn Thr
 50                  55                  60

Ala Asp Gln Cys Ala Asn Arg Cys Ile Arg Asn Lys Gly Leu Pro Phe
 65                  70                  75                  80

Thr Cys Lys Ala Phe Val Phe Asp Lys Ala Arg Lys Cys Leu Trp
                85                  90                  95

Phe Pro Phe Asn Ser Met Thr Ser Gly Val Lys Lys Glu Phe Gly His
            100                 105                 110

Glu Phe Asp Leu Tyr Glu Asn Lys Asp Tyr Ile Arg Asn Cys Ile Ile
        115                 120                 125

Gly Lys Gly Gly Ser Tyr Lys Gly Thr Val Ser Ile Thr Lys Ser Gly
    130                 135                 140

Ile Lys Cys Gln Pro Trp Asn Ser Met Ile Pro His Glu His Ser Phe
145                 150                 155                 160

Leu Pro Ser Ser Tyr Arg Gly Lys Asp Leu Gln Glu Asn Tyr Cys Arg
                165                 170                 175

Asn Pro Arg Gly Glu Glu Gly Gly Pro Trp Cys Phe Thr Ser Asn Pro
            180                 185                 190

Glu Val Arg Tyr Glu Val Cys Asp Ile Pro Gln Cys Ser Glu Val Glu
        195                 200                 205

Cys Met Thr Cys Asn Gly Glu Ser Tyr Arg Gly Pro Met Asp His Thr
    210                 215                 220

Glu Ser Gly Lys Ile Cys Gln Arg Trp Asp Arg Gln Thr Pro His Arg
225                 230                 235                 240

His Lys Phe Leu Pro Glu Arg Tyr Pro Asp Lys Gly Phe Asp Asp Asn
                245                 250                 255

Tyr Cys Arg Asn Pro Asp Gly Lys Pro Arg Pro Trp Cys Tyr Thr Leu
```

-continued

```
                260                 265                 270
Asp Pro Asp Thr Pro Trp Glu Tyr Cys Ala Ile Lys Met Cys Ala His
            275                 280                 285
Ser Thr Met Asn Asp Thr Asp Val Pro Met Glu Thr Thr Glu Cys Ile
290                 295                 300
Gln Gly Gln Gly Glu Gly Tyr Arg Gly Thr Ile Asn Ser Ile Trp Asn
305                 310                 315                 320
Gly Val Pro Cys Gln Arg Trp Asp Ser Gln Tyr Pro His Gln His Asp
                325                 330                 335
Ile Thr Pro Glu Asn Phe Lys Cys Lys Asp Leu Arg Glu Asn Phe Cys
            340                 345                 350
Arg Asn Pro Asp Gly Ala Glu Ser Pro Trp Cys Phe Thr Thr Asp Pro
            355                 360                 365
Asn Ile Arg Val Gly Tyr Cys Ser Gln Ile Pro Lys Cys Asp Val Ser
            370                 375                 380
Ser Gly Gln Asp Cys Tyr Arg Gly Asn Gly Lys Asn Tyr Met Gly Asn
385                 390                 395                 400
Leu Ser Lys Thr Arg Ser Gly Leu Thr Cys Ser Met Trp Glu Lys Asn
                405                 410                 415
Met Glu Asp Leu His Arg His Ile Phe Trp Glu Pro Asp Ala Ser Lys
            420                 425                 430
Leu Asn Lys Asn Tyr Cys Arg Asn Pro Asp Asp Ala His Gly Pro
            435                 440                 445
Trp Cys Tyr Thr Gly Asn Pro Leu Ile Pro Trp Asp Tyr Cys Pro Ile
            450                 455                 460
Ser Arg Cys Glu Gly Asp Thr Thr Pro Thr Ile Val Asn Leu Asp His
465                 470                 475                 480
Pro Val Ile Ser Cys Ala Lys Thr Lys Gln Leu Arg Val Val Asn Gly
                485                 490                 495
Ile Pro Thr Arg Thr Asn Val Gly Trp Met Val Ser Leu Lys Tyr Arg
            500                 505                 510
Asn Lys His Ile Cys Gly Gly Ser Leu Ile Lys Glu Ser Trp Ile Leu
            515                 520                 525
Thr Ala Arg Gln Cys Phe Pro Ser Arg Asn Lys Asp Leu Lys Asp Tyr
            530                 535                 540
Glu Ala Trp Leu Gly Ile His Asp Val His Gly Arg Gly Asp Glu Lys
545                 550                 555                 560
Arg Lys Gln Val Leu Asn Val Ser Gln Leu Val Tyr Gly Pro Glu Gly
                565                 570                 575
Ser Asp Leu Val Leu Leu Lys Leu Ala Arg Pro Ala Val Leu Asp Asp
            580                 585                 590
Phe Val Ser Thr Ile Asp Leu Pro Asn Tyr Gly Cys Thr Ile Pro Glu
            595                 600                 605
Lys Thr Thr Cys Ser Val Tyr Gly Trp Gly Tyr Thr Gly Ser Ile Asn
            610                 615                 620
Ser Asp Gly Leu Leu Arg Val Ala His Leu Tyr Ile Met Gly Asn Glu
625                 630                 635                 640
Lys Cys Ser Gln Tyr His Gln Gly Lys Val Thr Leu Asn Glu Ser Glu
                645                 650                 655
Ile Cys Ala Gly Ala Glu Asn Ile Val Ser Gly Pro Cys Glu Gly Asp
            660                 665                 670
Tyr Gly Gly Pro Leu Val Cys Glu Gln His Lys Met Arg Met Val Leu
            675                 680                 685
```

```
Gly Val Ile Val Pro Gly Arg Gly Cys Ala Ile Pro Asn Arg Pro Gly
    690             695                 700

Ile Phe Val Arg Val Ala Tyr Tyr Ala Lys Trp Ile His Lys Ile Ile
705                 710                 715                 720

Leu Thr Tyr Lys Ile Pro Gln Ser
                725

<210> SEQ ID NO 3
<211> LENGTH: 2172
<212> TYPE: DNA
<213> ORGANISM: Felis sp.
<220> FEATURE:
<221> NAME/KEY: CDS
<222> LOCATION: (1)..(2172)

<400> SEQUENCE: 3
```

| | |
|---|---:|
| atg tgg gtg acc aaa ctt ctt cca gtc ctg ctg ctg cag cac gtc ctc<br>Met Trp Val Thr Lys Leu Leu Pro Val Leu Leu Leu Gln His Val Leu<br>1               5                    10                15 | 48 |
| ctc cac ctc ctt ctg ctt ccc atc ccc tat gca gaa gga cag aag aaa<br>Leu His Leu Leu Leu Leu Pro Ile Pro Tyr Ala Glu Gly Gln Lys Lys<br>            20                    25                    30 | 96 |
| aga aga aac aca ctt cat gaa ttc aaa aag tca gca aag act act cta<br>Arg Arg Asn Thr Leu His Glu Phe Lys Lys Ser Ala Lys Thr Thr Leu<br>        35                    40                    45 | 144 |
| att aaa gaa gac cca tta ctg aag ata aaa aca aaa aaa atg aac act<br>Ile Lys Glu Asp Pro Leu Leu Lys Ile Lys Thr Lys Lys Met Asn Thr<br>50                      55                    60 | 192 |
| gca gac caa tgt gcc aat aga tgt att agg aat aaa gga ctt cca ttc<br>Ala Asp Gln Cys Ala Asn Arg Cys Ile Arg Asn Lys Gly Leu Pro Phe<br>65                70                    75                    80 | 240 |
| act tgc aag gcc ttt gtt ttt gat aaa gca agg aaa cga tgc ctc tgg<br>Thr Cys Lys Ala Phe Val Phe Asp Lys Ala Arg Lys Arg Cys Leu Trp<br>                85                    90                    95 | 288 |
| ttc cct ttc aat agc atg aca agt gga gtg aaa aaa gag ttt ggt cat<br>Phe Pro Phe Asn Ser Met Thr Ser Gly Val Lys Lys Glu Phe Gly His<br>                    100                  105                110 | 336 |
| gaa ttc gat ctc tat gaa aac aaa gac tac att aga aac tgc atc att<br>Glu Phe Asp Leu Tyr Glu Asn Lys Asp Tyr Ile Arg Asn Cys Ile Ile<br>              115                  120                125 | 384 |
| ggc aaa gga ggt agc tac aag gga aca gta tct atc act aag agt ggc<br>Gly Lys Gly Gly Ser Tyr Lys Gly Thr Val Ser Ile Thr Lys Ser Gly<br>130                   135                  140 | 432 |
| atc aaa tgc cag cct tgg aat tct atg ata cca cat gaa cac agc tat<br>Ile Lys Cys Gln Pro Trp Asn Ser Met Ile Pro His Glu His Ser Tyr<br>145                   150                  155                160 | 480 |
| cgg ggt aaa gac cta cag gaa aac tac tgt cga aat cct cga ggg gaa<br>Arg Gly Lys Asp Leu Gln Glu Asn Tyr Cys Arg Asn Pro Arg Gly Glu<br>                    165                  170                175 | 528 |
| gaa ggg gga cct tgg tgt ttc aca agc aat cca gag gta cgc tac gaa<br>Glu Gly Gly Pro Trp Cys Phe Thr Ser Asn Pro Glu Val Arg Tyr Glu<br>                    180                  185                190 | 576 |
| gtc tgt gac att cct cag tgt tca gaa gtt gaa tgc atg acc tgc aat<br>Val Cys Asp Ile Pro Gln Cys Ser Glu Val Glu Cys Met Thr Cys Asn<br>              195                  200                205 | 624 |
| ggg gaa agt tat cga ggt ccc atg gat cat aca gaa tca ggc aag att<br>Gly Glu Ser Tyr Arg Gly Pro Met Asp His Thr Glu Ser Gly Lys Ile<br>210                   215                  220 | 672 |
| tgt cag cgc tgg gat cgt cag aca cca cac cgg cac aaa ttc ttg cca<br>Cys Gln Arg Trp Asp Arg Gln Thr Pro His Arg His Lys Phe Leu Pro | 720 |

```
                225                 230                 235                 240 gaa aga tat ccc gac aag ggc ttt gat gat aat tat tgc cgc aat cct        768
Glu Arg Tyr Pro Asp Lys Gly Phe Asp Asp Asn Tyr Cys Arg Asn Pro
                245                 250                 255 gat ggc aag ccg agg cca tgg tgc tat act ctt gac cct gac acc ccc        816
Asp Gly Lys Pro Arg Pro Trp Cys Tyr Thr Leu Asp Pro Asp Thr Pro
                260                 265                 270 tgg gag tac tgt gca att aaa atg tgc gct cac agt act atg aat gac        864
Trp Glu Tyr Cys Ala Ile Lys Met Cys Ala His Ser Thr Met Asn Asp
            275                 280                 285 aca gat gtg cct atg gaa aca act gaa tgc att cag ggt caa gga gaa        912
Thr Asp Val Pro Met Glu Thr Thr Glu Cys Ile Gln Gly Gln Gly Glu
        290                 295                 300 ggt tac cgg ggc acc atc aac tcc atc tgg aat gga gtt cca tgt cag        960
Gly Tyr Arg Gly Thr Ile Asn Ser Ile Trp Asn Gly Val Pro Cys Gln
305                 310                 315                 320 cgt tgg gat tcc cag tat cct cac cag cat gac ata act cct gaa aat       1008
Arg Trp Asp Ser Gln Tyr Pro His Gln His Asp Ile Thr Pro Glu Asn
                325                 330                 335 ttc aag tgc aag gac cta cga gaa aat ttt tgc cga aat cca gat gga       1056
Phe Lys Cys Lys Asp Leu Arg Glu Asn Phe Cys Arg Asn Pro Asp Gly
                340                 345                 350 gct gag tca ccc tgg tgt ttt acc act gat cca aac atc cga gtt ggc       1104
Ala Glu Ser Pro Trp Cys Phe Thr Thr Asp Pro Asn Ile Arg Val Gly
            355                 360                 365 tac tgc tcc caa att cca aaa tgt gat gtg tcg agt gga caa gat tgt       1152
Tyr Cys Ser Gln Ile Pro Lys Cys Asp Val Ser Ser Gly Gln Asp Cys
        370                 375                 380 tat cgt ggg aat ggc aaa aat tat atg ggc aat tta tcc aaa aca cga       1200
Tyr Arg Gly Asn Gly Lys Asn Tyr Met Gly Asn Leu Ser Lys Thr Arg
385                 390                 395                 400 tct gga cta aca tgt tca atg tgg gag aag aac atg gaa gac tta cac       1248
Ser Gly Leu Thr Cys Ser Met Trp Glu Lys Asn Met Glu Asp Leu His
                405                 410                 415 agg cat atc ttc tgg gaa cca gat gct agt aag ctg aat aag aat tac       1296
Arg His Ile Phe Trp Glu Pro Asp Ala Ser Lys Leu Asn Lys Asn Tyr
                420                 425                 430 tgc cgg aat cct gat gat gat gcc cat ggc ccc tgg tgt tac acg gga       1344
Cys Arg Asn Pro Asp Asp Asp Ala His Gly Pro Trp Cys Tyr Thr Gly
            435                 440                 445 aat cct ctc att cca tgg gat tat tgt cct att tct cgt tgt gaa ggt       1392
Asn Pro Leu Ile Pro Trp Asp Tyr Cys Pro Ile Ser Arg Cys Glu Gly
        450                 455                 460 gat acc aca cct aca ata gtc aat tta gac cat ccc gta ata tct tgt       1440
Asp Thr Thr Pro Thr Ile Val Asn Leu Asp His Pro Val Ile Ser Cys
465                 470                 475                 480 gcc aaa aca aaa caa ctg cga gtt gta aat gga atc cca acg cgg aca       1488
Ala Lys Thr Lys Gln Leu Arg Val Val Asn Gly Ile Pro Thr Arg Thr
                485                 490                 495 aat gta gga tgg atg gtt agt ttg aaa tac aga aat aaa cat atc tgt       1536
Asn Val Gly Trp Met Val Ser Leu Lys Tyr Arg Asn Lys His Ile Cys
                500                 505                 510 gga gga tca ttg ata aag gaa agt tgg att ctt acc gca aga caa tgt       1584
Gly Gly Ser Leu Ile Lys Glu Ser Trp Ile Leu Thr Ala Arg Gln Cys
            515                 520                 525 ttc cct tct cga aac aaa gac ttg aaa gat tac gaa gct tgg ctt ggg       1632
Phe Pro Ser Arg Asn Lys Asp Leu Lys Asp Tyr Glu Ala Trp Leu Gly
        530                 535                 540 att cat gat gtc cac gga aga gga gat gag aaa cgc aaa cag gtt cta       1680
```

```
Ile His Asp Val His Gly Arg Gly Asp Glu Lys Arg Lys Gln Val Leu
545                 550                 555                 560 aat gtg tcc cag ctg gta tat ggg cct gaa ggg tca gat ctg gta tta    1728
Asn Val Ser Gln Leu Val Tyr Gly Pro Glu Gly Ser Asp Leu Val Leu
                565                 570                 575 ctg aag ctt gct agg cct gct gtc ctg gat gat ttt gtt agt aca att    1776
Leu Lys Leu Ala Arg Pro Ala Val Leu Asp Asp Phe Val Ser Thr Ile
            580                 585                 590 gat tta cct aat tat gga tgc acc att cct gaa aaa acc act tgc agt    1824
Asp Leu Pro Asn Tyr Gly Cys Thr Ile Pro Glu Lys Thr Thr Cys Ser
        595                 600                 605 gtt tat ggc tgg ggt tat act gga tca atc aac tct gat ggt cta tta    1872
Val Tyr Gly Trp Gly Tyr Thr Gly Ser Ile Asn Ser Asp Gly Leu Leu
    610                 615                 620 cga gta gca cat ctc tat att atg ggg aat gag aaa tgc agc caa tac    1920
Arg Val Ala His Leu Tyr Ile Met Gly Asn Glu Lys Cys Ser Gln Tyr
625                 630                 635                 640 cat caa ggg aag gtg act ctg aat gag tct gaa ata tgt gca ggt gcc    1968
His Gln Gly Lys Val Thr Leu Asn Glu Ser Glu Ile Cys Ala Gly Ala
                645                 650                 655 gaa aat att gtg tca gga cca tgt gag gga gat tat ggt ggc cca ctt    2016
Glu Asn Ile Val Ser Gly Pro Cys Glu Gly Asp Tyr Gly Gly Pro Leu
            660                 665                 670 gtt tgt gaa caa cat aaa atg aga atg gtc ctt ggt gtc att gtt cct    2064
Val Cys Glu Gln His Lys Met Arg Met Val Leu Gly Val Ile Val Pro
        675                 680                 685 ggt cgt gga tgt gcc att cca aat cgt cct ggc att ttt gtc cga gta    2112
Gly Arg Gly Cys Ala Ile Pro Asn Arg Pro Gly Ile Phe Val Arg Val
    690                 695                 700 gca tat tat gca aaa tgg ata cac aaa att ata tta aca tat aag ata    2160
Ala Tyr Tyr Ala Lys Trp Ile His Lys Ile Ile Leu Thr Tyr Lys Ile
705                 710                 715                 720 cca cag tca tag                                                    2172
Pro Gln Ser <210> SEQ ID NO 4
<211> LENGTH: 723
<212> TYPE: PRT
<213> ORGANISM: Felis sp.

<400> SEQUENCE: 4

Met Trp Val Thr Lys Leu Leu Pro Val Leu Leu Gln His Val Leu
 1               5                  10                  15

Leu His Leu Leu Leu Pro Ile Pro Tyr Ala Glu Gly Gln Lys Lys
             20                  25                  30

Arg Arg Asn Thr Leu His Glu Phe Lys Lys Ser Ala Lys Thr Thr Leu
            35                  40                  45

Ile Lys Glu Asp Pro Leu Leu Lys Ile Lys Thr Lys Lys Met Asn Thr
        50                  55                  60

Ala Asp Gln Cys Ala Asn Arg Cys Ile Arg Asn Lys Gly Leu Pro Phe
65                  70                  75                  80

Thr Cys Lys Ala Phe Val Phe Asp Lys Ala Arg Lys Arg Cys Leu Trp
                85                  90                  95

Phe Pro Phe Asn Ser Met Thr Ser Gly Val Lys Lys Glu Phe Gly His
            100                 105                 110

Glu Phe Asp Leu Tyr Glu Asn Lys Asp Tyr Ile Arg Asn Cys Ile Ile
        115                 120                 125

Gly Lys Gly Gly Ser Tyr Lys Gly Thr Val Ser Ile Thr Lys Ser Gly
```

-continued

```
            130                 135                 140
Ile Lys Cys Gln Pro Trp Asn Ser Met Ile Pro His Glu His Ser Tyr
145                 150                 155                 160

Arg Gly Lys Asp Leu Gln Glu Asn Tyr Cys Arg Asn Pro Arg Gly Glu
                165                 170                 175

Glu Gly Gly Pro Trp Cys Phe Thr Ser Asn Pro Glu Val Arg Tyr Glu
                180                 185                 190

Val Cys Asp Ile Pro Gln Cys Ser Glu Val Glu Cys Met Thr Cys Asn
                195                 200                 205

Gly Glu Ser Tyr Arg Gly Pro Met Asp His Thr Glu Ser Gly Lys Ile
210                 215                 220

Cys Gln Arg Trp Asp Arg Gln Thr Pro His Arg His Lys Phe Leu Pro
225                 230                 235                 240

Glu Arg Tyr Pro Asp Lys Gly Phe Asp Asp Asn Tyr Cys Arg Asn Pro
                245                 250                 255

Asp Gly Lys Pro Arg Pro Trp Cys Tyr Thr Leu Asp Pro Asp Thr Pro
                260                 265                 270

Trp Glu Tyr Cys Ala Ile Lys Met Cys Ala His Ser Thr Met Asn Asp
                275                 280                 285

Thr Asp Val Pro Met Glu Thr Thr Glu Cys Ile Gln Gly Gln Gly Glu
290                 295                 300

Gly Tyr Arg Gly Thr Ile Asn Ser Ile Trp Asn Gly Val Pro Cys Gln
305                 310                 315                 320

Arg Trp Asp Ser Gln Tyr Pro His Gln His Asp Ile Thr Pro Glu Asn
                325                 330                 335

Phe Lys Cys Lys Asp Leu Arg Glu Asn Phe Cys Arg Asn Pro Asp Gly
                340                 345                 350

Ala Glu Ser Pro Trp Cys Phe Thr Thr Asp Pro Asn Ile Arg Val Gly
                355                 360                 365

Tyr Cys Ser Gln Ile Pro Lys Cys Asp Val Ser Ser Gly Gln Asp Cys
370                 375                 380

Tyr Arg Gly Asn Gly Lys Asn Tyr Met Gly Asn Leu Ser Lys Thr Arg
385                 390                 395                 400

Ser Gly Leu Thr Cys Ser Met Trp Glu Lys Asn Met Glu Asp Leu His
                405                 410                 415

Arg His Ile Phe Trp Glu Pro Asp Ala Ser Lys Leu Asn Lys Asn Tyr
                420                 425                 430

Cys Arg Asn Pro Asp Asp Ala His Gly Pro Trp Cys Tyr Thr Gly
                435                 440                 445

Asn Pro Leu Ile Pro Trp Asp Tyr Cys Pro Ile Ser Arg Cys Glu Gly
450                 455                 460

Asp Thr Thr Pro Thr Ile Val Asn Leu Asp His Pro Val Ile Ser Cys
465                 470                 475                 480

Ala Lys Thr Lys Gln Leu Arg Val Val Asn Gly Ile Pro Thr Arg Thr
                485                 490                 495

Asn Val Gly Trp Met Val Ser Leu Lys Tyr Arg Asn Lys His Ile Cys
                500                 505                 510

Gly Gly Ser Leu Ile Lys Glu Ser Trp Ile Leu Thr Ala Arg Gln Cys
                515                 520                 525

Phe Pro Ser Arg Asn Lys Asp Leu Lys Asp Tyr Glu Ala Trp Leu Gly
                530                 535                 540

Ile His Asp Val His Gly Arg Gly Asp Glu Lys Arg Lys Gln Val Leu
545                 550                 555                 560
```

-continued

```
Asn Val Ser Gln Leu Val Tyr Gly Pro Glu Gly Ser Asp Leu Val Leu
                565                 570                 575

Leu Lys Leu Ala Arg Pro Ala Val Leu Asp Asp Phe Val Ser Thr Ile
            580                 585                 590

Asp Leu Pro Asn Tyr Gly Cys Thr Ile Pro Glu Lys Thr Thr Cys Ser
        595                 600                 605

Val Tyr Gly Trp Gly Tyr Thr Gly Ser Ile Asn Ser Asp Gly Leu Leu
    610                 615                 620

Arg Val Ala His Leu Tyr Ile Met Gly Asn Glu Lys Cys Ser Gln Tyr
625                 630                 635                 640

His Gln Gly Lys Val Thr Leu Asn Glu Ser Glu Ile Cys Ala Gly Ala
                645                 650                 655

Glu Asn Ile Val Ser Gly Pro Cys Glu Gly Asp Tyr Gly Gly Pro Leu
            660                 665                 670

Val Cys Glu Gln His Lys Met Arg Met Val Leu Gly Val Ile Val Pro
        675                 680                 685

Gly Arg Gly Cys Ala Ile Pro Asn Arg Pro Gly Ile Phe Val Arg Val
    690                 695                 700

Ala Tyr Tyr Ala Lys Trp Ile His Lys Ile Ile Leu Thr Tyr Lys Ile
705                 710                 715                 720

Pro Gln Ser
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 5
tctttcascc mggcatctcc                                           20

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 6
tgtgtatcca ttttgcataa tatgctactc                                30

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 7
gcatctccts cagagggatc                                           20

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 8

-continued tggcacatcc acgaccagga acaatgacac          30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 9
tggcacatcc acgaccagga acaatgacac          30

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic

<400> SEQUENCE: 10
ctcmagtagt tgtyttagga ttg          23

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic

<400> SEQUENCE: 11
cctacaggaa aactactgtc gaaatcctcg          30

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 12
tggrtgcttc arayacact          19

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic

<400> SEQUENCE: 13
ggatccgcca gcgcgtccag cagcacc          27

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic

<400> SEQUENCE: 14
tgggtgcttc aaatacactt acatcag          27

<210> SEQ ID NO 15
<211> LENGTH: 30
<212> TYPE: DNA
<213> ORGANISM: Artificial Sequence

```
<220> FEATURE:
<223> OTHER INFORMATION: Description of Artificial Sequence: Synthetic

<400> SEQUENCE: 15
atgtgggtga ccaaacttct tccagtcctg                                         30

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic

<400> SEQUENCE: 16
ctatgactgt ggtatcttat atgttaat                                           28

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 17
ctatcactaa gagtggcatc                                                    20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 18
ggaatgtcac agacttcgta g                                                  21
```

FELINE HEPATOCYTE GROWTH FACTOR

CROSS REFERENCE

This application is a divisional of 10/297,158, now U.S. Pat. No. 7,125,688, granted on Oct. 24, 2006 and filed Dec. 2, 2002, which claims the benefit of priority from Japanese Patent Application No. 2000/163185 filed May 31, 2000 through PCT/JP01/04559 filed May 30, 2001; the contents of each of which are incorporated by reference herein in its entirety.

FIELD OF THE INVENTION

The present invention relates to a feline hepatocyte growth factor, a 5 amino acids-deleted feline hepatocyte growth factor thereof, and genes encoding these factors.

BACKGROUND OF THE INVENTION

Human hepatocyte growth factor (hereinafter refer to as "HGF") has been purified as a liver regeneration factor. A gene encoding this factor has also been cloned and the sequence has been determined. Initially, HGF had been considered to function only for hepatocyte growth. However, subsequent studies have revealed that HGF does not only function for growth and regeneration of a hepatocyte, but also has strong effects of protecting from damage and of regenerating an organ on lung, kidney, blood vessel and heart tissues. Moreover, HGF also has very varied functions, for example it shows a strong antitumor activity against certain types of cancer.

From a study using various types of cultured cells, it has been found that HGF functions as a growth promoting factor, a mobility promoting factor, a morphogenesis promoting factor and a tumor suppressing factor. Moreover, expression of HGF enhances in organs, such as the lung and the kidney, responses to hepatopathy, and regeneration of the liver is promoted by a mechanism via the blood. It has been confirmed that, in other organs such as the kidney or the lung also, regeneration of such organs is promoted by the same mechanism. All of these HGF functions are biological activities essential for the construction and maintenance of tissues and organs, and so it is expected that HGF would be clinically significant when applied as specific medicines for intractable organ diseases for which basic treatment methods have not yet been established. Furthermore, a gene therapy for chronic arteriosclerosis obliterans of diabetes patients, which uses an HGF gene, is being attempted.

It has been reported that HGF has many variants generated by alternative splicing. It has been shown that, of these, a variant HGF which lacks 15 base pairs in the first kringle domain corresponding to a receptor binding site, that is, a variant HGF which lacks 5 amino acids, has a two or three times higher growth promoting activity on epithelium cells, when compared with ordinary HGF, and that this variant HGF has a different physiological action. It is hoped that this 15 base pairs-deleted HGF has a higher treatment effect on diseases mainly such as damaged epithelial tissues.

A mechanism for regenerating liver tissues by HGF will be described in detail. The expression of HGF mRNA is induced promptly in an interstitial cell, such as the Kupffer cell or the sinusoid endothelial cell in the liver, in response to various types of hepatopathies. HGF produced and secreted from interstitial cells acts on an epithelial cell such as a hepatocyte or biliary cell and promotes regeneration of the liver. Experiments have been carried out where recombinant HGF was administered to a disease model animal, and it has been reported that the recombinant HGF regenerated many types of organopathy. It has been reported that the tissues of many impaired organs such as the liver (e.g. hepatocirrhosis, hepatitis, fatty liver disease, etc.), the kidney (acute and chronic renal failure), the lung, the heart and the stomach, have been regenerated.

The full length of a human HGF gene (hereinafter, referred to as "hHGF") spans about 70 kb. The full length of mRNA, which is a transcribed product of the hHGF gene, is about 6 kb, and the length of a region encoding a protein in the mRNA is about 2.2 kb. The hHGF is initially synthesized as a single prepro-HGF consisting of 728 amino acids, and after 31 amino acids existing at the N-terminus are cleaved, a portion between the 494$^{th}$ Arg and the 495$^{th}$ Val is cleaved with protease, so that it becomes a mature molecule in which the α and β chains link with a single difulfide bond.

Thus far, HGF genes of human, mouse, rat and so on have been cloned, and the nucleotide sequences thereof have been determined.

With the recent trend of the aging of household pets, there occurs a problem regarding increases of various atrophic or regressive feline diseases, which are associated with aging. The development of pharmaceuticals directed towards such diseases, in which the regeneration of tissues are required, is considered to be important. Generally, these diseases often become chronic. Long-term administration of medicine is required to treat chronic diseases. However, if recombinant HGF proteins are administered to different species, the problem of antigenicity occurs and there may be a risk that long-term administration becomes impossible. Therefore, a recombinant feline HGF, which does not have the problem of antigenicity and can be administered for a long time, is required as a therapeutic agent for these chronic feline diseases.

OBJECT AND SUMMARY OF THE INVENTION

It is an object of the present invention to provide a feline HGF, a 5 amino acids-deleted HGF, and genes encoding the feline HGF.

As a result of intensive studies by the present inventors directed toward the above object, they have succeeded in determining the sequence of a feline HGF gene using the RT-PCR method, thereby completing the present invention.

That is to say, the present invention is a recombinant protein of the following (a) or (b):

(a) a protein having an amino acid sequence shown in SEQ ID NO: 2 or 4; and (b) a protein having an amino acid sequence comprising a deletion, substitution or addition of one or several amino acids with respect to the amino acid sequence shown in SEQ ID NO: 2 or 4, and having a feline HGF activity.

In addition, the present invention is a gene encoding the following protein (a) or (b):

(a) a protein having an amino acid sequence shown in SEQ ID NO: 2 or 4; and (b) a protein having an amino acid sequence comprising a deletion, substitution or addition of one or several amino acids with respect to the amino acid sequence shown in SEQ ID NO: 2 or 4, and having a feline HGF activity.

Moreover, the present invention is a gene comprising the DNA of the following (c) or (d):

(c) DNA comprising a nucleotide sequence shown in SEQ ID NO: 1 or 3; and (d) DNA hybridizing with the DNA comprising the nucleotide sequence shown in SEQ ID NO: 1 or 3 under stringent conditions, and encoding a protein having a feline HGF activity.

Further, the present invention is a recombinant vector comprising one of the above-described genes.

Furthermore, the present invention is a transformant comprising the above-described recombinant vector.

Still further, the present invention is a method for producing a feline HGF, which is characterized in that it comprises culturing the above-described transformant and collecting a feline HGF from the obtained culture.

Still further, the present invention is a reagent for detecting a feline HGF which comprises at least a fragment of the above-described genes.

Still further, the present invention is a pharmaceutical composition comprising the above recombinant feline HGF, and the above-described pharmaceutical composition is used for the treatment of liver diseases, kidney diseases, lung diseases, bone diseases, digestive diseases, cardiocirculatory diseases or cranial nerve diseases.

This specification includes part or all of the contents as disclosed in the specification and/or drawings of Japanese Patent Application No. 2000-163185, which is a priority document of the present application.

THE BEST MODE FOR CARRYING OUT THE INVENTION

The present invention will be explained in detail below.

The present invention relates to a gene encoding a feline HGF (feline HGF; hereinafter, referred to as fHGF), which has a strong ability to regenerate impaired organs and is expected to be clinically applied to intractable organ diseases for which basic treatment methods have not yet been established; a recombinant fHGF; a recombinant vector comprising the gene; a transformant comprising the recombinant vector; a method of producing the fHGF; a method of detecting the fHGF; and a pharmaceutical composition comprising the fHGF. Moreover, the present invention relates to a gene encoding a variant fHGF (dfHGF), which lacks 15 base pairs in the first kringle domain corresponding to a receptor binding site, that is, a variant fHGF which lacks 5 amino acids, that is known to have a two or three times higher growth promoting activity on epithelium cells when compared with ordinary HGF and to have a different physiological action. Furthermore, the present invention relates to a recombinant dfHGF, recombinant vector comprising the gene, transformant comprising the recombinant vector, method of producing the dfHGF, method of detecting the dfHGF and pharmaceutical composition comprising the dfHGF.

The present inventors extracted and purified RNA, and designed several primers, which are considered to be specific for HGF. Then, they carried out RT-PCR to obtain several DNA fragments. Some of the thus obtained DNA fragments were cloned in plasmid vectors to determine the nucleotide sequences. Based on the determined nucleotide sequences, overlapping portions of each DNA fragment were eliminated, and the sequence of a fHGF gene of interest was determined. Moreover, a 15 base pair-deleted fHGF gene generated by alternative splicing was isolated, and the sequence was determined. The sequences of the genes of the present invention were determined by this method.

1. Cloning of Gene of the Present Invention (1) Preparation of cDNA Clone by RT-PCR Examples of sources of mRNA include tissues such as the liver, the kidney, the lung, the brain, the thymus and the leukocyte of cat. Preparation of mRNA can be carried out by any conventional method. For example, the total RNA is extracted from the above-mentioned tissues or cells by the guanidium thocyanate-phenol method or the like, and poly (A)$^+$RNA(mRNA) is then obtained by the affinity column method or batch method, in which oligo dT-cellulose, poly U-sepharose or the like is used. Moreover, poly(A)$^+$RNA may further be fractioned by the sucrose density gradient centrifugation method.

Using the thus obtained mRNA as a template, a single strand cDNA is synthesized with oligo dT primers and reverse transcriptase. To obtain a clone comprising the DNA sequence of interest, for example, a degenerate sense primer and a degenerate antisense primer for the amino acid sequence of the already obtained HGF protein family are synthesized, PCR is carried out using these primers, and the obtained fragment is incorporated into a suitable cloning vector to prepare a recombinant vector. Using this recombinant vector, *Escherichia coli* or the like is transformed, and then, using tetracycline resistance or ampicillin resistance as an index, a transformant is selected so as to obtain a clone comprising a part or the full length of the sequences of fHGF and dfHGF genes. Moreover, in the present invention, primers are not limited to the above-described primers.

Herein, transformation of *Escherichia coli* can be carried out by the Hanahan's method [Hanahan, D.: J. Mol. Biol. 166: 557-580 (1983)], which comprises adding a recombinant vector to a competent cell which is prepared by allowing calcium chloride, magnesium chloride or rubidium chloride to coexist. Where a plasmid is used as a vector, the plasmid should contain a drug resistance gene, which is resistant to tetracycline, ampicillin and so on. Moreover, a cloning vector other than a plasmid such as a λ phage (λgt11, etc.) can also be used.

(2) Determination of Nucleotide Sequence of DNA Fragment

The nucleotide sequences of a single or multiple isolated clones comprising the above-described DNA fragment are determined, using a PCR product as a template. Determination of a nucleotide sequence can be carried out by any known methods such as the Maxam-Gilbert chemical modification method or the dideoxynucleotide chain termination method in which M13 phage is used, but in general, sequencing is carried out using an automatic nucleotide sequencer (e.g. a Model 310 fluorescent sequencer produced by Applied Biosystems). Based on nucleotide sequence information on a single or multiple DNA fragments derived from fHGF or a single or multiple DNA fragments derived from dfHGF, which are obtained by the above-described method, the nucleotide sequence of fHGF or dfHGF of interest is determined by eliminating overlapping portions.

The nucleotide sequence of the fHGF gene of the present invention is shown in SEQ ID NO: 1, the amino acid sequence of the fHGF of the present invention is shown in SEQ ID NO: 2, the nucleotide sequence of the 15 base pairs-deleted fHGF gene of the present invention is shown in SEQ ID NO: 3, and the amino acid sequence of the 5 amino acids-deleted fHGF of the present invention is shown in SEQ ID NO: 4. However, as long as a protein having this amino acid sequence exhibits a fHGF activity, the amino acid sequence may comprise a mutation such as a deletion, substitution or addition of at least one, preferably one or several amino acids.

For example, an amino acid sequence shown in SEQ ID NO: 2 or 4 may comprise a deletion of at least one, preferably one or several amino acids (for example, 1 to 10 amino acids, more preferably 1 to 5 amino acids). Or, an amino acid sequence shown in SEQ ID NO: 2 or 4 may comprise an addition of at least one, preferably one or several amino acids (for example, 1 to 10 amino acids, more preferably 1 to 5 amino acids). Otherwise, an amino acid sequence shown in SEQ ID NO: 2 or 4 may comprise a substitution of at least one, preferably one or several amino acids (for example, 1 to 10 amino acids, more preferably 1 to 5 amino acids) by other amino acids.

Moreover, the gene of the present invention also includes DNA hybridizing with the above gene under the following conditions and encoding a protein having a fHGF activity. That is to say, the conditions herein mean that, using a filter on which DNA is fixed, hybridization is carried out at 68° C. under 0.7 to 1.0 M NaCl followed by washing at 68° C. with 0.1 to 2×SSC solution (1×SSC consisting of 150 mM NaCl and 15 mM sodium citrate).

Furthermore, the present invention also includes RNA corresponding to the above DNA, or an RNA hybridizing with the RNA under stringent conditions and encoding a protein having a fHGF activity.

Introduction of a mutation into a gene can be carried out by any known technique such as the Kunkel method or the Gapped Duplex method, or an equivalent method. For example, the introduction of a mutation can be carried out, using a kit for introducing a mutation (e.g. Mutant-K (TAKARA), Mutant-G (TAKARA)), with which a site-directed mutagenesis is applied, or an LA PCR in vitro Mutagenesis series kit (TAKARA).

The gene of the present invention has a nucleotide sequence corresponding to the amino acid sequence of a fHGF.

Once the nucleotide sequence of the gene of the present invention is determined, the gene of the present invention can then be obtained by chemical synthesis, by PCR in which cDNA is used as a template, or by performing hybridization, using a DNA fragment having the nucleotide sequence as a probe.

2. Preparation of Recombinant Vector and Transformant (1) Preparation of Recombinant Vector The recombinant vector of the present invention can be obtained by ligating (inserting) the gene of the present invention into a suitable vector. The vector into which the gene of the present invention is inserted is not to be particularly limited provided that it can replicate in a host, and examples of such a vector include plasmid DNA, phage DNA and others.

Examples of plasmid DNA include a plasmid derived from *Escherichia coli* (e.g. pBR322, pBR325, pUC118, pUC119, pUC18, pUC19, etc.), a plasmid derived from *Bacillus subtilis* (e.g. pUB110, pTP5, etc.), a plasmid derived from yeast (e.g. YEp13, YEp24, YCp50, etc.) and others. Examples of phage DNA include λ phage (Charon4A, Charon21A, EMBL3, EMBL4, λgt10, λgt11, λZAP, etc.). Moreover, an animal virus such as a retrovirus or vaccinia virus, or an insect virus vector such as a baculovirus, can also be used.

To insert the gene of the present invention into a vector, a method is applied, in which initially, purified DNA is cleaved with appropriate restriction enzymes, and the obtained DNA fragment is then inserted into the restriction site or the multicloning site of a suitable vector DNA to ligate the fragment to the vector.

It is necessary that the gene of the present invention is incorporated into a vector so that the functions of the gene are exhibited. Thus, not only can a promoter and the gene of the present invention, but also a cis-element such as an enhancer, a splicing signal, a poly(A) addition signal, a selective marker or a ribosome binding sequence (SD sequence), can be ligated to the vector of the present invention as desired. Examples of a selective marker include a dihydrofolate reductase gene, an ampicillin resistance gene, a neomycin resistance gene and others.

(2) Preparation of Transformant

The transformant of the present invention can be obtained by introducing the recombinant vector of the present invention into a host, so that the gene of interest can express therein. Herein, a host is not to be particularly limited provided that it allows the DNA of the present invention to be expressed. Examples of such a host include bacteria such as *Escherichia* sp. *Escherichia coli*, *Bacillus* sp. *Bacillus subtilis*, and *Pseudomonas* sp. *Pseudomonas putida*; yeast such as *Saccharomyces cerevisiae* and *Shizosaccharomyces pombe*; animal cells such as a COS cell and a CHO cell; and insect cells such as S121 and sf9. Moreover, an insect body itself from a silkworm, *Autographa california* or the like can also be used as a host.

Where a bacterium such as *Escherichia coli* is used as the host, it is preferable that the recombinant vector of the present invention be able to autonomously replicate in the bacterium and that the recombinant vector comprises a promoter, a ribosome binding sequence, the gene of the present invention and a transcription termination sequence. Moreover, a gene controlling the promoter may also be incorporated.

Examples of *Escherichia coli* include *Escherichia coli* DH1 and *Escherichia coli* JM109, and examples of B. subtilis include *Bacillus subtilis* and so on, but examples are not limited thereto.

Any promoter can be used provided that it can be expressed in a host such as *Escherichia coli*. For example, promoters derived from *Escherichia coli* or phage such as a trp promoter, a lac promoter, a $P_L$ promoter or a $P_R$ promoter can be used. An artificially designed and modified promoter such as a tac promoter may also be used.

A method for introducing a recombinant vector into a bacterium is not to be particularly limited provided that it is a method for introducing DNA into a bacterium. For example, a method of using calcium ion [Cohen, S. N. et al.: Proc. Natl. Acad. Sci., USA, 69: 2110(1972)], the electroporation method, etc. can be used.

Where yeast is used as the host, for example, *Saccharomyces cerevisiae*, *Schizosaccharomyces pombe* or *Pichia pastoris* is used. In the use of yeast as a host, any promoter can be used to such an extent that it can be expressed in yeast, and examples of such a promoter include a gal1 promoter, a gal10 promoter, a heat shock protein promoter, an MFα1 promoter, a PH05 promoter, a PGK promoter, a GAP promoter, an ADH promoter, an AOX1 promoter and others.

A method for introducing a recombinant vector into yeast is not particularly to be limited provided that it is a method for introducing DNA into yeast, and examples of such a method include the electroporation method [Becker, D. M. et al.: Methods. Enzymol., 194: 182 (1990)], the spheroplast method [Hinnen, A et al.: Proc. Natl. Acad. Sci., USA, 75: 1929 (1978)], the lithium acetate method [Itoh, H.: J. Bacteriol., 153: 163 (1983)] and others.

Where an animal cell is used as the host, a monkey cell COS-1 or COS-7, Vero, a Chinese hamster ovary cell (CHO cell), a mouse L cell, a rat GH3, a human FL cell, etc. can be used. Examples of promoters used include an SRα promoter, an SV40 promoter, an LTR promoter, a CMV promoter and others, and further a human cytomegalovirus immediate early gene promoter or the like may also be used. Examples of methods of introducing a recombinant vector into an animal cell include the electroporation method, the calcium phosphate method, the lipofection method and others.

Where an insect cell is used as a host, an S121 cell, an Sf9 cell, etc. can be used. Examples of a method of introducing a recombinant vector into an insect cell include the calcium phosphate method, the lipofection method, the electroporation method, etc.

Further, where an insect body itself is used, a silkworm, *Autographa california* and so on can be used. A method of introducing a recombinant virus into an insect body includes natural infection.

(3) Production of Protein of the Present Invention

The protein of the present invention is a protein having an amino acid sequence encoded by the fHGF gene or the 15 base pairs-deleted fHGF gene of the present invention, or a protein having an amino acid sequence comprising the above-described mutation introduced into at least one amino acid relative to the above amino acid sequence and having a fHGF activity. It should be noted that the protein of the present invention is also referred to as a fHGF protein, and a 15 base pairs-deleted type thereof is also referred to as a 5 amino acids-deleted fHGF protein.

The fHGF protein of the present invention can be obtained by culturing the above-described transformant and collecting the fHGF from the cultured product. The term a "cultured product" is herein used to mean any of a culture supernatant, a cultured cell or cultured cell body, and a homogenized product of the cell or cell body.

The culture of the transformant of the present invention is carried out according to common methods used for the culture of a host.

As a medium for culturing a transformant obtained while using a microorganism such as *Escherichia coli* or yeast as a host, either a natural medium or a synthesized medium can be used to such an extent that the medium contains a carbon source, a nitrogen source, inorganic salts and others, which can be assimilated by the microorganism, and can be efficiently utilized in the culture of the transformant.

Examples of a carbon source include carbohydrates such as glucose, fructose, sucrose or starch, organic acids such as acetic acid or propionic acid, and alcohols such as ethanol and propanol.

Examples of a nitrogen source include an inorganic or organic ammonium salt such as ammonia, ammonium chloride, ammonium sulfate, ammonium acetate or ammonium phosphate, other nitrogen-containing compounds, peptone, meat extract, corn steep liquor and others.

Examples of an inorganic product include potassium primary phosphate, potassium secondary phosphate, magnesium phosphate, magnesium sulfate, sodium chloride, ferrous sulfate, manganese sulfate, copper sulfate, calcium carbonate and others.

Generally, culture is carried out at 37° C. under aerobic conditions such as shaking culture or aeration and agitation culture. Control of the pH of the medium is carried out using an inorganic or organic acid, or an alkaline solution.

During culture, an antibiotic such as ampicillin or tetracycline may be added to the medium as necessary.

For culturing a microorganism transformed with an expression vector comprising an inducible promoter, an inducer may be added to the medium as necessary. For example, when a microorganism transformed with an expression vector comprising a Lac promoter is cultured, isopropyl-β-D-thiogalactopyranoside (IPTG) or the like may be added to the medium, and when a microorganism transformed with an expression vector comprising a trp promoter, indoleacetic acid (IAA) or the like may be added thereto.

For culturing a transformant obtained by using an animal cell as a host, commonly used RPMI 1640 medium, DMEM medium or a medium obtained by adding fetal bovine serum or the like to these media, can be used.

Generally, culture is carried out at 37° C. for 1 to 30 days in the presence of 5% $CO_2$. During culture, an antibiotic such as kanamycin or penicillin may be added to the medium as necessary.

Where the protein of the present invention is produced inside a cell body or cell after culture, a fHGF protein is extracted by homogenizing the cell body or the cell. Where the protein of the present invention is produced outside a cell body or cell, the culture solution is used as is, or the cell body or the cell is eliminated by centrifugal separation or the like. After that, the protein of the present invention can be isolated and purified from the above culture by biochemical methods commonly used for isolation and purification of proteins, used either singly or in combination, e.g. ammonium sulfate precipitation, gel chromatography, ion exchange chromatography, affinity chromatography and others.

3. Method of Detecting fHGF Using the Gene of the Present Invention and Detection Reagent (1) Use of the Gene of the Present Invention or Portion Thereof as Probe In the present invention, a probe hybridizing with the above-described DNA or RNA and specifically detecting the DNA or the RNA is also provided as a reagent for detecting a fHGF. This probe is labeled with a commonly used radioisotope (e.g. $^{32}P$, $^{35}S$), an enzyme (e.g. digoxigenin, fluororescein) or the like, and the labeled probe is then hybridized specifically with the DNA or the RNA by a common blotting analysis, In situ hybridization or the like, thereby detecting the DNA or the RNA.

DNA or RNA used as a probe in the present invention has at least a portion of the nucleotide sequence of the DNA which are shown in SEQ ID NO: 1 or 3 or a RNA corresponding to the DNA. The length of the probe is 200 to 300 nucleotides, but it may have an entire sequence and it is not particularly limited.

4. Pharmaceutical Composition Comprising the Recombinant fHGF of the Present Invention The recombinant fHGF or the 15 base pairs-deleted HGF thereof of the present invention is a recombinant fHGF or a 5 amino acids-deleted HGF thereof, which has been extracted and purified, or a recombinant fHGF or a 5 amino acids-deleted HGF thereof, which has been inserted into a plasmid or the like and allowed to translate inside the body of a cat. Such a factor is used as a pharmaceutical composition for the treatment of liver diseases such as fulminant hepatitis, acute hepatitis, hepatocirrhosis, liver fibrosis, fatty liver and liver cancer, kidney diseases such as acute renal failure, chronic renal failure/nephrosclerosis, renal transplantation and diabetic nephropathy, lung diseases such as acute pneumonia and lung fibrosis, bone diseases such as osteoarthritis deformans and arthritis rheumatica, digestive diseases such as gastric ulcer and diabetes (suppression of apoptosis of β cells of pancreas, promotion of insulin production), cardiovascular diseases such as myocardial infarction, hypertrophic/congestive cardiomyopathy and angiopathy (diabetic retinopathy, arteriosclerosis obliterans, etc.), and cranial nerve diseases such as cerebral infarction and Parkinson's disease.

The pharmaceutical composition of the present invention is particularly useful for the treatment of chronic feline diseases such as feline chronic renal failure, and this composition has no antigenic side effects and can be used for a long time.

The pharmaceutical composition of the present invention comprises a fHGF or a 5 amino acids-deleted HGF thereof or a salt thereof or a DNA fragment of a fHGF gene or dfHGF gene bound to a plasmid or the like to be translates inside the body of a cat with a pharmacologically acceptable carrier, diluent or excipient. The pharmaceutical composition of the present invention can be administered in various forms. Examples of such an administration form include orally administration using tablets, capsules, granules, powders or syrups, or parenterall administration using injection, drop or suppository. Such a composition is produced by any known method and comprises a carrier, a diluent and an excipient, which are commonly used in the pharmaceutical field. For example, as a carrier or excipient used for a tablet, lactose, magnesium stearate or the like is used. An injection is prepared by dissolving, suspending or emulsifying the fHGF or a salt thereof in a sterile aqueous or oily solution. Examples of aqueous solution used for an injection include a physiological salt solution and an isotonic solution containing glucose or another adjuvant, and the aqueous solution may be used in combination with an appropriate solution adjuvant such as alcohol, polyalcohol such as propylene glycol or a nonionic surfactant. Examples of the above-mentioned oily solution include sesame oil, soybean oil and so on, and the oily solution may be used in combination with a solution adjuvant such as benzyl benzoate or benzyl alcohol.

The dosage applied depends on symptom, age, body weight and others. In the case of oral administration, generally, it is approximately 0.001 mg to 1,000 mg per cat per day, and the pharmaceutical composition with the above dosage is administered all at once, or divided several times throughout a day. In contrast, in the case of parenteral administration, 0.001 mg to 1,000 mg of the pharmaceutical composition is administered per cat per day in the form of a subcutaneous injection, intramuscular injection or intravenous injection. Moreover, in the case of using a recombinant fHGF or recombinant dfHGF inserted into a plasmid and allowed to translate inside the body of a cat, 0.001 mg to 1,000 mg is administered per cat every several days, weeks or months in the form of a subcutaneous, intramuscular or intravenous injection.

BRIEF DISCRIPTION OF THE DRAWINGS

EXAMPLES

Figure 1:
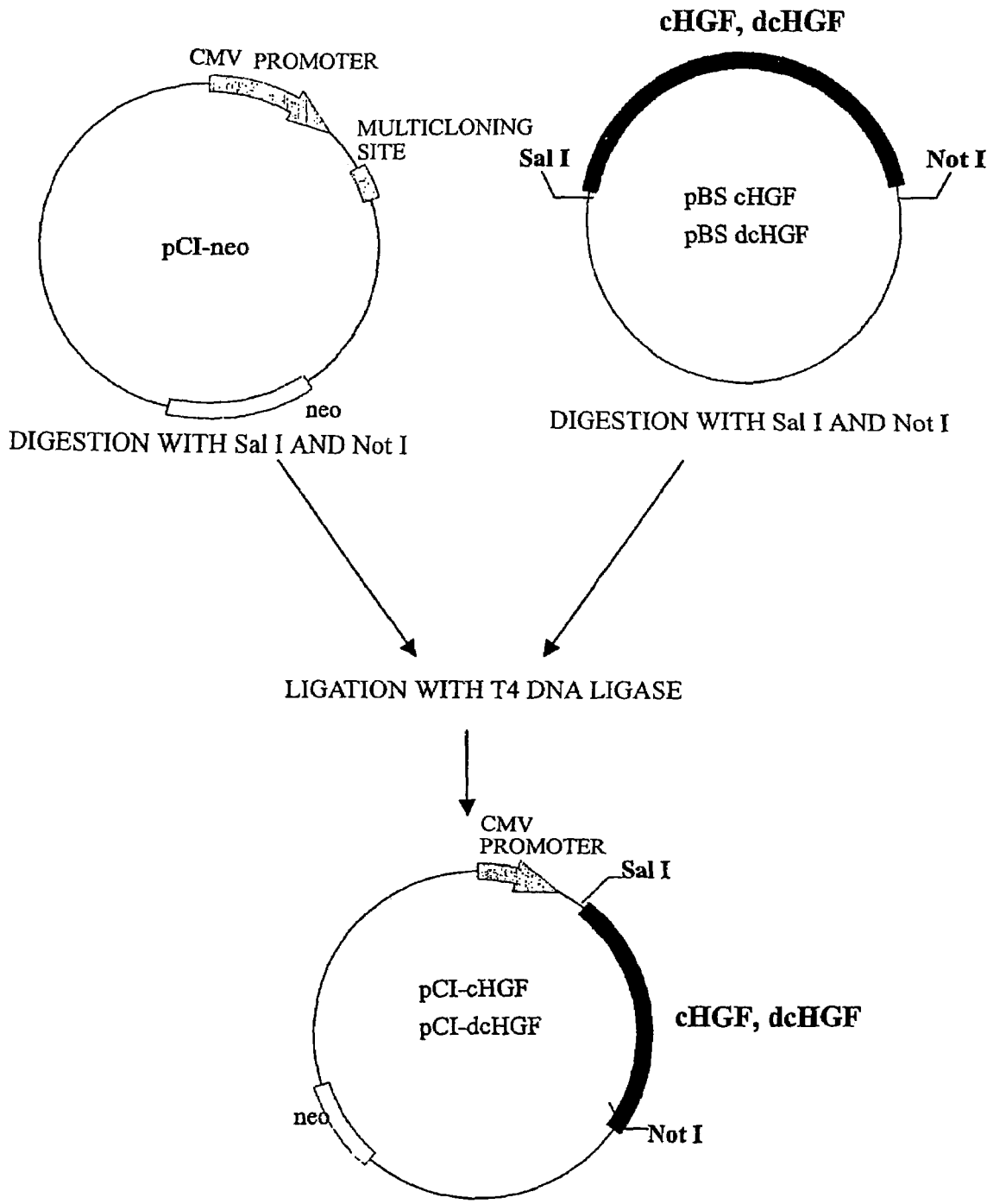
FIG. 1 shows the construction of recombinant fHGF and dfHGF vectors for the expression of a protein, which are used in COS1 cells and CHO cells in Example 2.

The present invention is further specifically described in the following examples. The examples are provided for illustrative purposes only, and are not intended to limit the technical scope of the invention.

Example 1

Isolation of fHGF Gene (a) Obtainment of DNA Fragment Derived from fHGF

The total RNA was extracted from a feline leukocyte by the guanidium thiocyanate-phenol method (Trizol Reagent (Gibco-BRL). Using 3' RACE System (Gibco-BRL), cDNA was synthesized from the extracted total RNA and was then subjected to an RT-PCR reaction.

To clone the full length of a fHGF protein translated region, initially, primers were designed on the basis of a nucleotide sequence corresponding to the 5' and 3' protein untranslated regions of a hHGF gene that had already been reported, and then amplification by the RT-PCR method was attempted. However, it was difficult to obtain an amplified product having the desired size. Thus, the protein translated region was divided into two regions and amplified by the RT-PCR method. After the amplified products were cloned into plasmid vectors, the sequences were determined. The nucleotide sequences obtained were combined to obtain the full length nucleotide sequence of fHGF protein translated region.

Amplification of 5' region of fHGF: Using an already reported nucleotide sequence as an index that is relatively well conserved over animal species such as human, mouse and rat, sense primers were designed in a 5' non-translated region. Antisense primers were designed using sequence in a protein translated region well conserved above as an index in the same way as the above-mentioned. It was difficult to amplify the desired fragment in a single PCR. Thus, nested PCR was attempted using the first PCR product as a template to obtain the amplified product having the desired size. A reaction solution having a composition set forth below was used for the PCR reaction. After a reaction was carried out at 94° C. for 2 minutes, the following cycle was repeated 30 times: 94° C. for 1 minute, 55° C. for 1 minute and 72° C. for 2 minutes. Finally, a reaction was carried out at 72° C. for 5 minutes. Thereafter the temperature of the reacted solution was maintained at 4° C.

Composition of reaction solution: 1× PCR buffer, 0.2 mM dNTP, 0.005 units/µl Taq polymerase (TaKaRa EX Taq), 0.5 µM each of the following primers:

```
Sense primer:
                                        (SEQ ID NO:5)
5' TCTTTCA(C/G)CC(A/C)GGCATCTCC 3'

Antisense primer:
                                        (SEQ ID NO:6)
5' TGTGTATCCATTTTGCATAATATGCTACTC 3'

Nested sense primer:
```

```
                                                    (SEQ ID NO:7)
    5' GCATCTCCT(C/G)CAGAGGGATC 3'

Nested antisense primer:
                                                    (SEQ ID NO:8)
    5' TGGCACATCCACGACCAGGAACAATGACAC 3'
```

Amplification of 3' region of fHGF: In the same way as in the amplification of 5' region, primers were designed using nucleotide sequence well conserved over animal species as an index, and the amplified products were obtained by the PCR method. Since it was difficult to amplify the desired fragments in a single PCR, nested PCR was attempted in the same way as the amplification of 5' region. The condition of the PCR was the same to that mentioned above except that the primers were different.

```
    Sense primer:
                                                    (SEQ ID NO:9)
    5' TGGCACATCCACGACCAGGAACAATGACAC 3'

Antisense primer:
                                                    (SEQ ID NO:10)
    5' CTC(C/A)AGTAGTTGT(C/T)TTAGGATTG 3'

Nested sense primer:
                                                    (SEQ ID NO:11)
    5' CCTACAGGAAAACTACTGTCGAAATCCTCG 3'

Nested antisense primer:
                                                    (SEQ ID NO:12)
    5' TGG(G/A)TGCTTCA(G/A)A(C/T)ACACT 3'
```

The obtained PCR product was subjected to agarose gel electrophoresis in the presence of ethidium bromide to confirm the size of the product. Products having measurable sizes were purified from the agarose gel (RECOCHIP (TaKaRa)), and ligated to the cloning site of a plasmid vector using T4DNA ligase (pGEM-T Easy Vector System (Promega)) so as to transform the host *Escherichia coli* JM109 (Promega). That is to say, after the *Escherichia coli* competent cell was mixed with the plasmid, the mixture was subjected to a temperature treatment on ice for 30 minutes, at 42° C. for 45 seconds, and on ice for 5 minutes. Then, the mixture was suspended in a High-competence broth (Nippon Gene Co., Ltd.) for incubation at 37° C. for 1 hour. Thereafter, it was placed on LB agar medium to which 50 µg/ml ampicillin was added, so that a transformed *Escherichia coli* colony was obtained. The transformed *Escherichia coli* was cultured at 37° C. overnight on LB medium (1% yeast extract, 0.5% tripton, 1% NaCl) to which 50 µg/ml ampicillin was added. After that, plasmid DNA was purified by alkali method, and the nucleotide sequence was determined (Espec Oligo Service Corp.). Incidentally, the final sequence was determined as follows. The nucleotide sequence analysis of 3 clones as well as the amplified products of 5' and 3' regions were performed and the sequence was finally determined when the nucleotide sequence of all 3 clones were completely the same among them.

(b) Analysis of Nucleotide Sequence of Inserted Fragment

The nucleotide sequences of the gene fragments obtained in (a) were combined using Genetyx-win ver. 4 software (Software Development) to obtain the entire nucleotide sequence of the fHGF gene protein translated region. The sequence is shown in SEQ ID NO: 1. This sequence consists of 2,187 bp. Using GENBANK/EMBL DNA Data Base, research was made for the nucleotide sequence shown in SED ID NO: 1. However, an identical sequence was not present. Accordingly, it was confirmed that DNA having this nucleotide sequence was an entirely new DNA. When homology searching was carried out using an online homology search program, BLAST and Genetyx-win ver. 4 software, the nucleotide sequence of SEQ ID NO: 1 showed high homology with the nucleotide sequences of the HGF genes of human (92.5%), mouse (88.2%) and rat (88.0%).

The amino acid sequence predicted from the nucleotide sequence of SEQ ID NO: 1 is shown in SEQ ID NO: 2. When the amino acid sequence was subjected to homology analysis as in the case with the nucleotide sequence, the amino acid sequence of SEQ ID NO: 2 showed high homology with the amino acid sequences of the HGFs of human (93.2%), mouse (93.3%) and rat (93.3%). From these results, it was strongly suggested that the nucleotide sequence of SEQ ID NO: 1 is a fHGF gene.

(c) Amplification of Full Length fHGF Protein Translated Region and Cloning

Primers were designed based on the nucleotide sequence of the fHGF obtained in (a) so as to amplify the full length protein translated region, and PCR was carried out using, as a template, cDNA derived from feline leukocyte. A reaction solution having a composition set forth below was used for the PCR reaction. After reaction was carried out at 94° C. for 2 minutes, the following reaction cycle was repeated 30 times: at 94° C. for 30 seconds, at 55° C. for 30 seconds and at 68° C. for 2 minutes. Finally, a reaction was carried out at 68° C. for 5 minutes, and the reaction solution temperature was maintained at 4° C.

Composition of reaction solution: 1×PCR buffer, 1 mM $MgSO_4$, 0.2 mM dNTP, 0.005 units/µl Taq polymerase KOD Plus (Toyobo), 0.5 µM each of the following primers:

```
    Sense primer:
                                                    (SEQ ID NO:13)
    5' GGATCCGCCAGCGCGTCCAGCAGCACC 3'

Antisense primer:
                                                    (SEQ ID NO:14)
    5' TGGGTGCTTCAAATACACTTACATCAG 3'

Nested sense primer:
                                                    (SEQ ID NO:15)
    5' ATGTGGGTGACCAAACTTCTTCCAGTCCTG 3'

Nested antisense primer:
                                                    (SEQ ID NO:16)
    5' CTATGACTGTGGTATCTTATATGTTAAT 3'
```

The obtained PCR product was subjected to agarose gel electrophoresis in the presence of ethidium bromide to confirm the size of the product. The products having the desired size were purified from the agarose gel (RECOCHIP (TaKaRa)), and ligated to pBluescript II KS(+) plasmid vector that was digested by EcoRV using DNA ligation kit ver.2 (TaKaRa). Then, the host *E.coli* was transformed as described in (a) to obtain *E.coli* colonies. The clone containing the desired insert fragment was selected by Insert Check Ready Kit (TOYOBO) and was cultured with LB medium overnight. Then, the plasmid DNA was purified (Wizard SV Minipreps DNA purification system (Promega)), and the sequence was confirmed (DSA-2000L (SHIMAZU)).

(d) Screening of 15 Base Pairs-deleted fHGF

To screen for 15 base pairs-deleted fHGF (hereinafter, dfHGF) due to alternative splicing in the first kringle domain, primers were designed so that the primers sandwich the deleted site. Then, using, as a template, an *Escherichia coli* colony transformed with vector DNA to which the full length protein translated region of a fHGF gene described in (c) was ligated, PCR was carried out using a reaction solution having a composition set forth below. After a reaction was carried out at 94° C. for 2 minutes, the following reaction cycle was repeated 30 times: at 94° C. for 30 seconds, at 55° C. for 30 seconds and at 72° C. for 30 seconds. Finally, a reaction was carried out at 72° C. for 5 minutes followed by maintaining the temperature at 4° C. Composition of reaction solution: 1×PCR buffer, 0.2 mM dNTP, 0.005 units/μl Taq polymerase (TaKaRa EX Taq), 0.5 μM each of the following primers:

```
Sense primer:
                                    (SEQ ID NO:17)
5' CTATCACTAAGAGTGGCATC 3'

Antisense primer:
                                    (SEQ ID NO:18)
5' GGAATGTCACAGACTTCGTAG 3'
```

The obtained PCR product was subjected to 4% agarose gel electrophoresis in the presence of ethidium bromide, and comparisons were made regarding the lengths of the amplified fragments of each clone. A clone having an amplified fragment shorter than a common fragment was selected. After the clone was cultured in LB medium overnight as stated above, plasmid DNA was purified and the nucleotide sequence was analyzed. The sequence is shown in SEQ ID NO: 3. The amino acid sequence predicted from the nucleotide sequence of SEQ ID NO: 3 is shown in SEQ ID NO: 4. The obtained dfHGF clone lacked 15 base pairs at a site corresponding to the first kringle domain, and as a result, 5 amino acids are missing. No differences were found for other nucleotide and amino acid sequences.

Example 2

Production of Recombinant fHGF Protein and Recombinant dfHGF Protein Using Mammalian Cell (a) Production of Recombinant Plasmid for Expression in Mammalian Cell Comprising DNA Encoding fHGF and dfHGF A one μg sample of the plasmid obtained in Example 1 (c) and (d) was digested with 10 units of restriction enzymes Sal I and Not I (TaKaRa) at 37° C. for 2 hours, and then subjected to agarose gel electrophoresis. Approximately 2.2 kbp DNA fragments of fHGF and dfHGF were purified using RECO-CHIP (TaKaRa). On the other hand, 1μg of an expression vector for a mammalian cell, pCI-neo Mammalian Expression Vector (Promega), was digested with 10 units of restriction enzymes Sal I and Not I (TaKaRa) at 37° C. for 2 hours, and then subjected to phenol chloroform treatment and ethanol precipitation according to a common technique so that the final concentration was maintained at 50 ng/μl. The above fHGF and dfHGF DNA fragments were ligated to an expression vector DNA of ligation kit ver. 2 (TaKaRa), and *Escherichia coli* was transformed by the above-described method. An *Escherichia coli* clone comprising fHGF and dfHGF genes was selected and plasmid DNA was purified (FIG. 1). Using an expression vector-derived sequence primer, T7-EEV (Promega), analysis of the nucleotide sequence was carried out and it was confirmed that the DNA fragments of fHGF and dfHGF were ligated as designed.

(b) Production of Recombinant fHGF and dfHGF Proteins in COS-1 Cell

Figure 2:
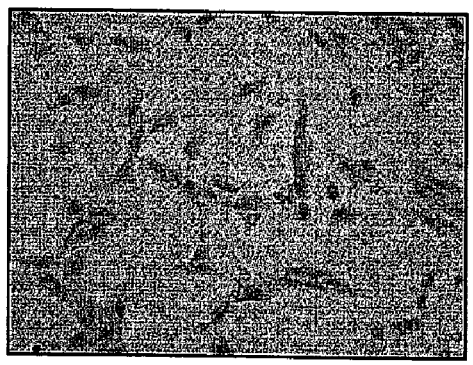
FIG. 2 shows the biological activity of fHGF and dfHGF produced in COS-1 cells in Example 2.
Figure 2:
Figure 2:

African green monkey COS-1 cells were maintained in E-MEM medium (Nissui Pharmaceutical Co., Ltd.) containing 10% fetal bovine serum (Moregate) and 0.3% Tryptose Phosphate broth (DIFCO) at 37° C. in the presence of 5% $CO_2$. A day before transformation, the COS-1 cells, which were proliferated to a confluent condition, were washed with PBS buffer, and then a trypsin-EDTA solution was added thereto and the mixture was left statically at room temperature for about 2 minutes. After the above medium was added thereto and the cells were well suspended, centrifugation was carried out at 1,200 rpm at 4° C. for 5 minutes. After the supernatant was eliminated, the remaining solution was suspended again in the medium, and the number of cells was counted according to a common technique. The number of cells was adjusted so that $8 \times 10^5$ cells were present in 5 ml of medium, and the cells were placed in a 60 mm-diameter petri dish (FALCON) and cultured at 37° C. overnight in the presence of 5% $CO_2$. The plasmid DNA for the expression of fHGF and dfHGF obtained in (a) was purified (Wizard SV Minipreps DNA purification system (Promega)) and adjusted so that the concentration was 1 μg/μl in distilled water. The introduction of the gene into the COS-1 cells were carried out using Lipofectamine 2000 Regent (GIBCO-BRL), and the gene transfer was carried out according to manufacturer's instructions. After the transfection of the gene, culture was carried out at 37° C. for 48 hours in the presence of 5% $CO_2$, so as to obtain the culture supernatant in which recombinant fHGF and dfHGF were produced. This culture supernatant was collected and the biological activity was determined in the manner described in Example 4. The enhanced cell mobility in MDCK cell was observed, and so it was confirmed that the recombinant fHGF and dfHGF proteins produced in COS-1 cells exhibited a biological activity (FIG. 2).

Figure 3:
FIG. 3 shows the biological activity of fHGF and dfHGF produced in CHO cells in Example 2.
Figure 3:
Figure 3:

(c) Production of Cell Line Which Stably Expresses the Recombinant fHGF and dfHGF Proteins Using a Chinese hamster CHO cells, a cell line which stably expresses the recombinant fHGF and dfHGF proteins were obtained. This CHO cells were maintainedin E-MEM medium (Nissui Pharmaceutical Co., Ltd.) containing 10% fetal bovine serum (Moregate) and 0.3% Tryptose Phosphate broth (DIFCO) at 37° C. in the presence of 5% $CO_2$. A day before transformation, the CHO cells, which wereproliferated to a confluent condition, were removed from the plate and resuspended in the medium by the above-described method, and the number of cells was counted. The number of cells was adjusted so that $1.2 \times 10^5$ cells were present in 500 μl of medium, and the cells were placed in a 24-well petri dish (FALCON) and cultured at 37° C. overnight in the presence of 5% $CO_2$. The plasmid DNA for expression of fHGF and dfHGF obtained in (a) was purified (Wizard SV Minipreps DNA purification system (Promega)) and adjusted so that the concentration was 1 μg/μl in distilled water. The transfection of the gene into CHO cells were carried out using Lipofectamine 2000 Regent (GIBCO-BRL), and the gene transfer operation was carried out according to an manufacturer's instructions. After the introduction of the gene, culture was carried out at 37° C. overnight in the presence of 5% $CO_2$. Thereafter, cells were removed by the above-described analysis and resuspended in 12 ml of the above-described amplification medium containing 600 μg/ml of GENETICIN (GIBCO BRL). A total of 500 μl of the suspension was poured into a 24-well Petri dish (FALCON), and cultured at 37° C. in the presence of 5% $CO_2$. The medium was replaced by a new medium approximately every 3 days, and culture was continuously carried out for about 2 weeks to obtain stable expression cell lines. The cell lines were screened from the culture supernatant by a limiting dilution method, so as to obtain cell lines with high recombinant fHGF and dfHGF protein producing activities. The thus obtained high production cell lines were cultured in the above amplification medium at 37° C. for several days in the presence of 5% $CO_2$, so as to obtain the culture supernatant in which recombinant fHGF and dfHGF proteins were produced. When this culture supernatant was collected and the biological activity was determined in the manner described in Example 4, enhanced cell mobility in MDCK cell was observed. Thus, it was confirmed that the recombinant fHGF and dfHGF proteins produced in a CHO cell exhibited a biological activity (FIG. 3).

Example 3

Figure 4:
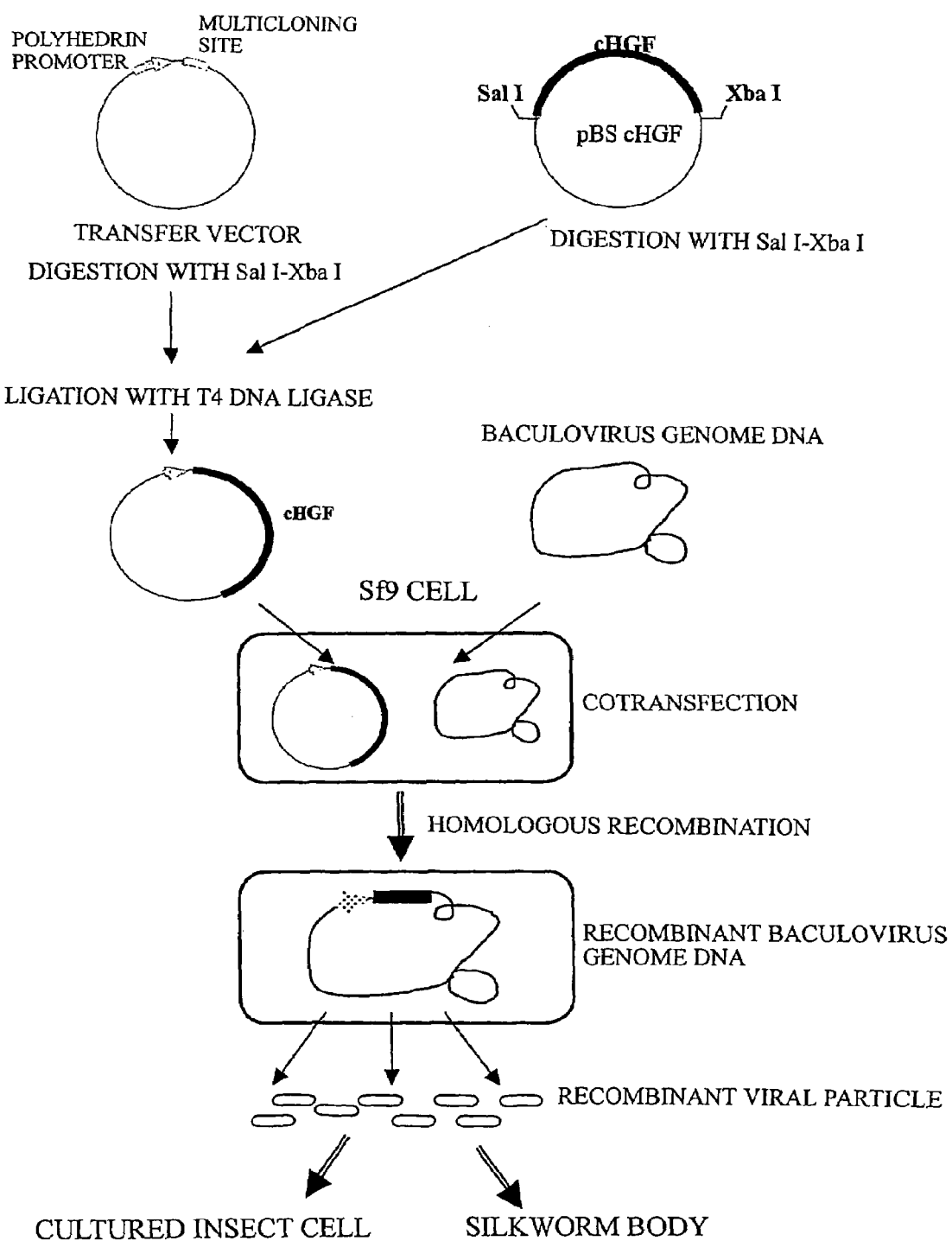
FIG. 4 shows the construction of a recombinant fHGF virus vector, for expression of a protein, which has been introduced into silkworm larvae and cultured insect cells in Example 3.
Figure 5:
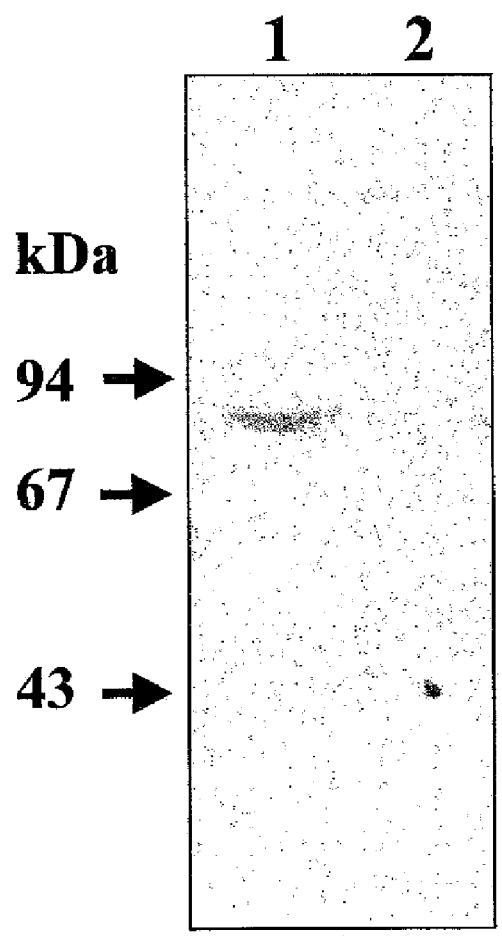
FIG. 5 shows the result of Western Blotting analysis of a recombinant fHGF produced in the silkworm larvae of Example 3.
Figure 6:
FIG. 6 shows the biological activity of a recombinant fHGF protein, which was produced in the silkworm larvae of Example 3.
Figure 6:
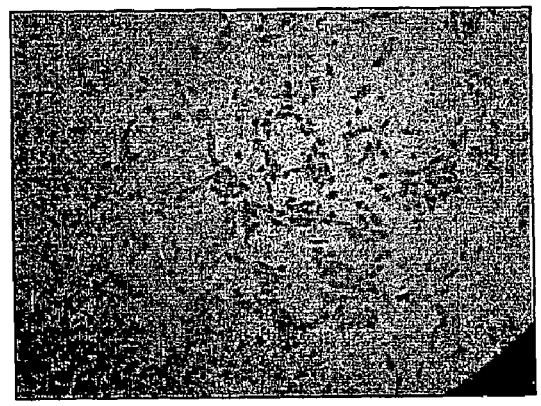
Figure 6:
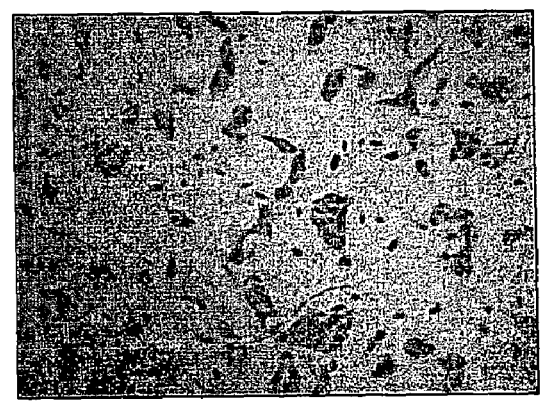

Production of Recombinant fHGF Protein in Silkworm Larvae and Cultured Insect Cells (a) Production of Recombinant fHGF Protein in Silkworm Larvae By using the Superworm Service of Katakura Industries Co., Ltd., a recombinant baculovirus transformed with DNA encoding fHGF and dfHGF was obtained using the plasmid vector obtained in Example 1 (c) (FIG. 4). The viral liquid of the obtained recombinant virus was inoculated into a silkwormlarvae, and after breeding for several days, the haemolymph was collected from the silkworm body. According to a common technique, the haemolymph fluid sample was subjected to SDS-polyacrylamide electrophoresis, and then to Western Blotting analysis so as to detect the recombinant fHGF protein at the position of a molecular weight of about 80,000 to 90,000 (FIG. 5). Further, when the biological activity was determined in the manner described in Example 4, enhanced cell mobility in MDCK cell was observed. Thus, it was confirmed that the recombinant fHGF and dfHGF protein produced in the silkworm larvae exhibited a biological activity (FIG. 6).

(b) Production of Recombinant fHGF Protein in Cultured Insect Cells

Figure 7:
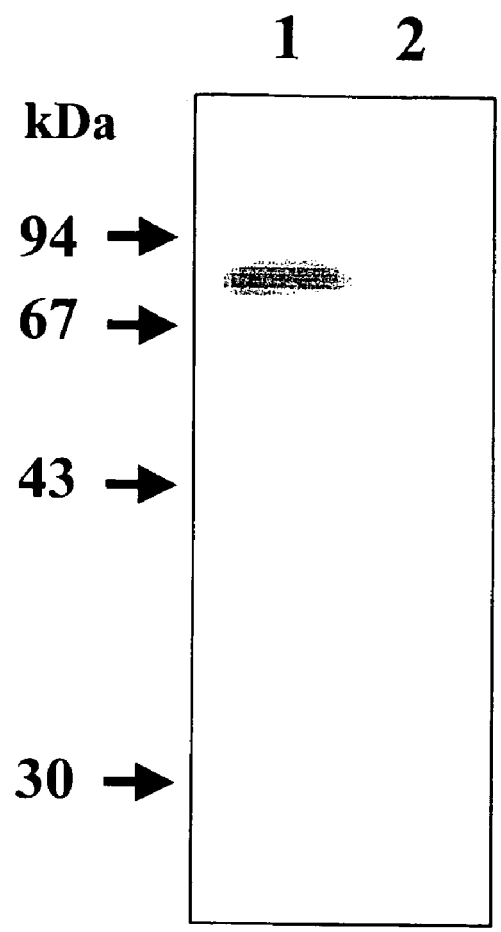
FIG. 7 shows the results of Western Blotting analysis of a recombinant fHGF, which is produced in the cultured insect cells of Example 3.
Figure 8:
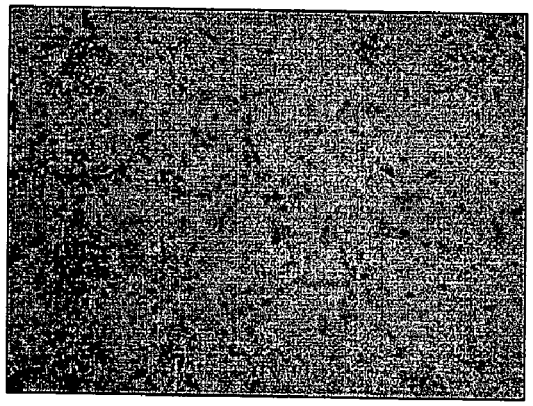
FIG. 8 shows the biological activity of a fHGF protein produced in the cultured insect cell of Example 3.
Figure 8:
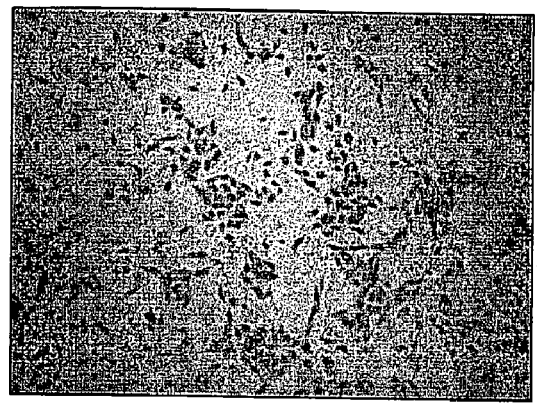
Figure 8:
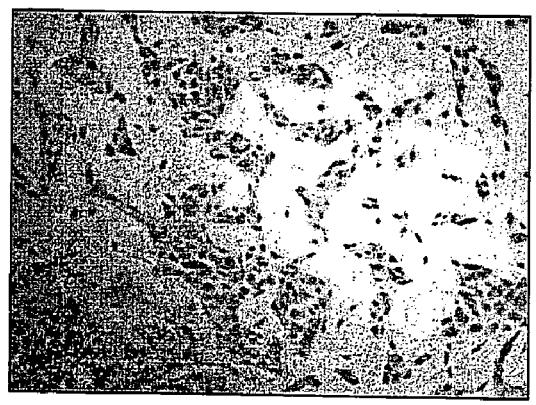

The above-obtained recombinant viral liquid was added to an Sf9 cell culture supernatant, and after culture for approximately 1 week, the culture supernatant was collected. The culture supernatant sample was subjected to SDS-polyacrylamide electrophoresis according to a common technique and then to Western Blotting analysis so as to detect the recombinant fHGF protein at the position of a molecular weight of about 80,000 to 90,000 (FIG. 7). Further, when the biological activity was determined in the manner described in Example 4, enhanced cell mobility in MDCK cell was observed. Thus, it was confirmed that the recombinant fHGF protein produced in the cultured insect cells exhibited a biological activity (FIG. 8).

Example 4

Determination of Biological Activity of Recombinant fHGF and dfHGF Proteins

The biological activity of recombinant fHGF and dfHGF proteins were determined by observing for enhancement of cell mobility in Madin-Darby Canine Kidney (MDCK) cells. The MDCK cells were maintained in the above expansion medium. The cells which proliferated to the confluent condition were harvested from the plate by the above-described method, and the number of cells was counted and then the cells were adjusted so that the number of the cells was $3 \times 10^4$ cells/ml. From this obtained cell suspension, 100 µl was dividely poured into each well of a 96-well plate (FALCON). Then, 50 µl each of the culture supernatant of the COS-1 cells, and the CHO cells, into which fHGF and dfHGF expression vectors obtained in Example 2 were introduced, was dividedly added to each well. Moreover, the haemolymph obtained in Example 3 was diluted with medium by a factor of 2,000, whereas the supernatant of a cultured insect cells were diluted with the same medium by a factor of 4. Then, 50 µl each of the diluents was further dividedly added to each well. Twenty-four hours after addition of the sample, a 1/10 volume of 25% glutaraldehyde solution (Wako Pure Chemical Industries, Ltd.) was added to fix the cells, and then the mobility and the form of the cells were observed by Giemsa stain under microscopy.

All publications, patents and patent applications cited herein are incorporated herein by reference in their entirety.

INDUSTRIAL APPLICABILITY

The present invention provides a fHGF, a 5 amino acids-deleted fHGF thereof, and genes encoding the fHGF and the 5 amino acids-deleted fHGF thereof. The recombinant fHGF and the 5 amino acids-deleted recombinant fHGF of the present invention are useful for treatment of chronic feline diseases such as feline liver or kidney diseases.

---

The invention claimed is:

1. An isolated recombinant protein having an amino acid sequence shown in SEQ ID NO: 2.

2. A pharmaceutical composition comprising the isolated recombinant protein according to claim 1.

3. The pharmaceutical composition according to claim 2, which is used for treatment of liver diseases, kidney diseases, lung diseases, bone diseases, digestive diseases, cardiocirculatory diseases or cranial nerve diseases.

* * * * *

UNITED STATES PATENT AND TRADEMARK OFFICE
CERTIFICATE OF CORRECTION

| | |
|---|---|
| PATENT NO. | : 7,425,536 B2 |
| APPLICATION NO. | : 11/450056 |
| DATED | : September 16, 2008 |
| INVENTOR(S) | : Masashi Miyake et al. |

It is certified that error appears in the above-identified patent and that said Letters Patent is hereby corrected as shown below:

At item (73) on the Title page of the patent, the assignee "Nippon Zenyaku Kogyo Ltd." should be "Nippon Zenyaku Kogyo Co., Ltd.".

Signed and Sealed this

Twenty-eighth Day of April, 2009

JOHN DOLL
*Acting Director of the United States Patent and Trademark Office*